United States Patent

Rafferty et al.

Patent Number: 5,760,035
Date of Patent: Jun. 2, 1998

[54] THERAPEUTIC AGENTS

[75] Inventors: Paul Rafferty; Gerald Bernard Tometzki. both of Nottingham. Great Britain

[73] Assignee: KNOLL Aktiengesellschaft, Ludwigshafen. Germany

[21] Appl. No.: 615,202

[22] PCT Filed: Sep. 16, 1994

[86] PCT No.: PCT/EP94/03121

§ 371 Date: Jun. 25, 1996

§ 102(e) Date: Jun. 25, 1996

[87] PCT Pub. No.: WO95/08535

PCT Pub. Date: Mar. 30, 1995

[30] Foreign Application Priority Data

Sep. 22, 1993 [EP] European Pat. Off. ........ 9319534

[51] Int. Cl.$^6$ .................. A01N 31/535; A01N 43/40; C07D 211/08; C07D 421/00
[52] U.S. Cl. .................. 514/235.5; 514/316; 514/317; 514/326; 514/331; 544/129; 546/191; 546/208; 546/227; 546/229; 546/232
[58] Field of Search .................. 546/208, 191, 546/227, 229, 232; 514/312, 235.5, 316, 326, 331, 317; 544/129

[56] References Cited

U.S. PATENT DOCUMENTS

| 3,531,487 | 9/1970 | Berger et al. | 260/293 |
| 4,027,028 | 5/1977 | Vincent et al. | 424/267 |
| 4,216,326 | 8/1980 | Zenitz | 546/226 |
| 4,304,911 | 12/1981 | Zenitz | 544/130 |
| 4,339,576 | 7/1982 | Zenitz | 544/130 |
| 4,348,401 | 9/1982 | Friebe et al. | 424/267 |
| 5,100,901 | 3/1992 | Sugimoto et al. | 514/319 |

FOREIGN PATENT DOCUMENTS

| 1082710 | 3/1976 | Canada . |
| 022 371 | 1/1981 | European Pat. Off. . |
| 296 560 | 12/1988 | European Pat. Off. . |
| 374 095 | 12/1988 | European Pat. Off. . |
| 306 375 | 3/1989 | European Pat. Off. . |
| 330 026 | 8/1989 | European Pat. Off. . |
| 343 307 | 11/1989 | European Pat. Off. . |
| 512 902 | 11/1992 | European Pat. Off. . |
| 515 240 | 11/1992 | European Pat. Off. . |
| 520 882 | 12/1992 | European Pat. Off. . |
| 526 342 | 2/1993 | European Pat. Off. . |
| 579 263 | 1/1994 | European Pat. Off. . |
| 63-154683 | 6/1988 | Japan . |
| 1036272 | 7/1966 | United Kingdom . |
| 1052302 | 12/1966 | United Kingdom . |
| 1194505 | 6/1970 | United Kingdom . |
| 92/02501 | 2/1992 | WIPO . |
| 92/02502 | 2/1992 | WIPO . |
| 94/02462 | 2/1994 | WIPO . |

Primary Examiner—C. Warren Ivy
Assistant Examiner—Raymond Covington
Attorney, Agent, or Firm—Keil & Weinkauf

[57] ABSTRACT

Compounds of formula I

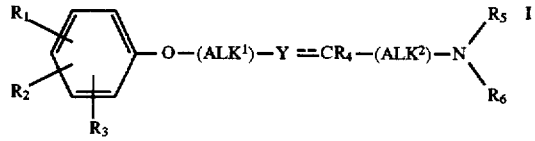

and pharmaceutically acceptable salts thereof in which $R_1$, $R_2$ and $R_3$ independently represent hydrogen, hydroxy, halo, alkyl or alkoxy;

$ALK^1$ represents a $C_{2-6}$ alkylene chain optionally substituted by one or more $C_{1-2}$ alkyl groups;

Y represents a piperidine ring which is attached through nitrogen to $ALK^1$;

$R_4$ represents hydrogen or a $C_{1-4}$ alkyl group; the broken line in --- represents a bond, or is absent and the free valency on Y is taken up by hydrogen and the free valency on $CR_4$ is taken up by hydrogen or a $C_{1-4}$ alkyl group;

$ALK^2$ is absent or represents a $C_{1-4}$ alkylene chain optionally substituted by one or more $C_{1-2}$ alkyl groups; and $R_5$ and $R_6$ independently represent hydrogen, alkyl, phenyl, alkyl (optionally substituted) or $R_5$ and $R_6$ together with the nitrogen atom to which they are attached represent a saturated 3–7 membered heterocyclic ring (with a proviso); are disclosed which are antiinflammatory, antiallergic and immunomodulatory agents. Compositions containing these compounds and processes to prepare these compounds are also disclosed.

14 Claims, No Drawings

THERAPEUTIC AGENTS

This is the National Stage Application of PCT/EP94/03121 filed Sep. 16, 1994, published as WO/95/08535 on Mar. 30, 1995.

This invention relates to novel substituted aminoalkyl-1-(aryloxyalkyl)piperidine compounds having therapeutic activity useful in treating conditions associated with inflammation, allergy or the immune system, to therapeutic compositions containing these novel compounds and to processes for preparing these novel compounds.

It is believed that, in response to an antiinflammatory stimulus, phospholipase enzymes are activated leading to the release of arachidonic acid from phospholipids. Existing non-steroidal antiinflammatory agents (NSAIA) are believed to act primarily by blocking the conversion of this released arachidonic acid into prostaglandins via the cyclo-oxygenase pathway of the arachidonic acid cascade. Many existing NSAIA are unsuitable for use by asthmatics. We have found a series of compounds which act to block the release of arachidonic acid from phospholipids. These compounds are indicated as useful antiinflammatory compounds with a potentially broader spectrum of activity than existing NSAIA, and potentially fewer gastro-intestinal side-effects. In addition the compounds may be useful in the treatment of asthma.

U.S. Pat. No. 4,027,028 discloses that compounds of formula A

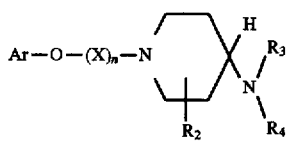

in which $R_2$ is a hydrogen or a lower alkyl radical; $R_3$ is the acyl residue of an organic alkylcarboxylic acid having up to 10 carbon atoms; $R_4$ is an optionally substituted phenyl radical; X is $C_{2-3}$ alkylene radical optionally substituted by one or more lower alkyl radicals; n is 1 or 2; and Ar is inter alia optionally substituted phenyl; are useful for treating hypertension. Compounds of formula A in which $R_3$ represents hydrogen are disclosed as intermediates but no pharmacological activity is reported for these compounds.

U.S. Pat. No. 4,348,401 discloses that compounds of formula B

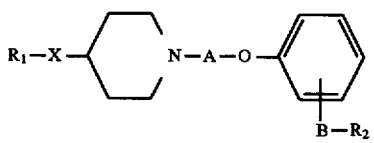

in which $R_1$ is a hydrogen atom, an acyl radical or an optionally substituted aryl radical; $R_2$ is a hydroxymethyl radical, a cyano group, an amidino group which is optionally substituted by hydroxyl, a 1H-tetrazol-5-yl radical or a —CO—$R_3$ radical. $R_3$ is a hydroxyl group, a lower alkoxy radical or an amino group which is optionally substituted by a 1H-tetrazol-1-yl radical; X is an imino group or an oxymethyl radical; A is an alkylene radical containing 2 to 4 carbon atoms and B is a valency bond or a 4-hydroxypyrimidin-2,5-diyl radical; have an anti-allergic action, especially due to their strongly anti-histaminic action. The compounds are also alleged to have anti-oedematous and anti-phlogistic effectiveness.

GB 1,052,302 discloses that compounds of formula C

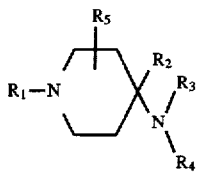

in which $R_1$ represents a straight- or branched-chain, saturated or unsaturated aliphatic hydrocarbon group containing at least two carbon atoms, a phenoxyalkyl group, an aralkyl group or an aralkenyl group; $R_2$ represents a straight- or branched-chain, saturated or unsaturated aliphatic hydrocarbon group, an aralkyl group, or an unsubstituted or substituted aromatic or aromatically unsaturated heterocyclic group; $R_3$ and $R_4$ which may be the same or different, each represents an alkyl or aralkyl group or, jointly, together with the adjacent nitrogen atom, represents a heterocyclic group which may contain a further hetero atom; and $R_5$ represents a hydrogen atom, or a lower alkyl group in the 3-position; exhibit analgesic activity and alleges that the compounds have spasmolytic, sedative and/or cough-soothing activity. However these compounds also exhibit cardiovascular activity which is undesirable.

EP 520,882 discloses the use of 4-aminomethyl-1-[2-(4-fluorophenoxy)ethyl]piperidine and 3-aminomethyl-1-[2-(2-methoxyphenoxy)ethyl]piperidine as chemical intermediates. No pharmacological activity is reported for these compounds.

EP 526,342 discloses the use of 4-(2-aminoethyl)-1-[2-(4-fluorophenoxy)ethyl]piperidine as a chemical intermediate. No pharmacological activity is reported for this compound.

Japanese Laid Open Patent Application No. 63-154683 (1988) discloses that certain pyridazinones are useful as heart stimulants. This application generically discloses intermediate compounds of formula D

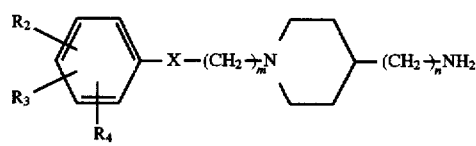

in which $R_2$, $R_3$ and $R_4$ independently represent hydrogen, a $C_{1-5}$ alkoxy group or hydroxy; m and n are each whole numbers from 0–4 and X is oxygen, sulphur, N($R_5$) (in which $R_5$ is hydrogen or a $C_{1-5}$ alkoxy group) or a single bond with the proviso that m is only 0 when X is a single bond. No specific examples are given of compounds of formula D in which X represents oxygen and no pharmacological activity is reported for compounds of formula D.

The present invention provides novel compounds of formula I

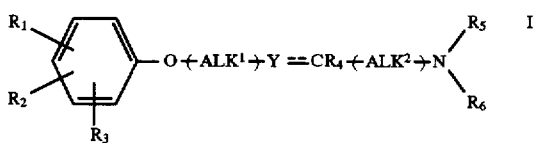

and pharmaceutically acceptable salts thereof in which $R_1$, $R_2$ and $R_3$ independently represent hydrogen, hydroxy, halo, a $C_{1-6}$ alkyl group (optionally substituted by one or more halogen atoms) or a $C_{1-6}$ alkoxy group (optionally substituted by one or more halogen atoms);

ALK$^1$ represents a $C_{2-6}$ alkylene chain optionally substituted by one or more $C_{1-2}$ alkyl groups;

Y represents a piperidine ring which is attached through nitrogen to $ALK^1$;

$R_4$ represents hydrogen or a $C_{1-4}$ alkyl group;

the broken line in === represents a bond, so that a double bond connects Y and $CR_4$, or is absent and the free valency on Y is taken up by hydrogen and the free valency on $CR_4$ is taken up by hydrogen or a $C_{1-4}$ alkyl group;

$ALK^2$ is absent or represents a $C_{1-4}$ alkylene chain optionally substituted by one or more $C_{1-2}$ alkyl groups; and $R_5$ and $R_6$ independently represent hydrogen, a $C_{1-6}$ alkyl group, a phenyl $C_{1-4}$ alkyl group (in which the phenyl ring is optionally substituted by one or more of the following: a $C_{1-4}$ alkyl group, a $C_{1-4}$ alkoxy group, halo or trifluoromethyl) or $R_5$ and $R_6$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups;

excluding 4-aminomethyl-1-[2-(4-fluorophenoxy)ethyl]piperidine, 4-(2-aminoethyl)-1-[2-(4-fluorophenoxy)ethyl]piperdine and 3-aminomethyl-1-[2-(2-methoxyphenoxy)ethyl]piperidine.

It will be understood that a group containing a chain of three or more carbon atoms may be straight or branched, for example propyl includes n-propyl and isopropyl and butyl includes n-butyl, sec-butyl, isobutyl and tert-butyl.

A preferred group of compounds of formula I is represented by formula II

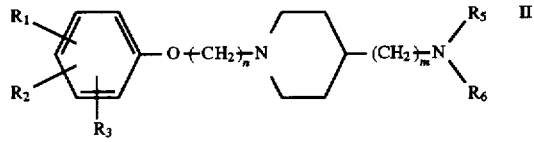

and pharmaceutically acceptable salts thereof in which $R_1$, $R_2$ and $R_3$ independently represent hydrogen, hydroxy, halo (for example bromo, chloro or fluoro), trifluoromethyl, a $C_{1-4}$ alkyl group (for example methyl, ethyl, propyl or butyl) or a $C_{1-4}$ alkoxy group (for example methoxy, ethoxy, propoxy or butoxy);

n=2–4 and m=1–3;

$R_5$ represents hydrogen, a $C_{1-4}$ alkyl group (for example methyl, ethyl, propyl or butyl) or a phenyl $C_{1-4}$ alkyl group [(in which the phenyl ring is optionally substituted by one or more of the following: a $C_{1-4}$ alkyl group, a $C_{1-4}$ alkoxy group or halo) for example benzyl or phenethyl]; and $R_6$ represents a $C_{1-4}$ alkyl group (for example methyl, ethyl, propyl or butyl) or a phenyl $C_{1-4}$ alkyl group [(in which the phenyl ring is optionally substituted by one or more of the following: a $C_{1-4}$ alkyl group, a $C_{1-4}$ alkoxy group or halo) for example benzyl or phenethyl];

or $R_5$ and $R_6$ together with the nitrogen atom to which they are attached represent a pyrrolidine ring, a piperidine ring or a morpholine ring.

A more preferred group of compounds of formula I is represented by formula III

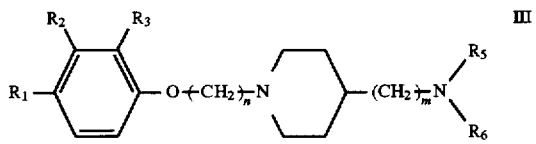

and pharmaceutically acceptable salts thereof in which $R_1$ represents hydrogen, halo, a $C_{1-4}$ alkyl group or a $C_{1-4}$ alkoxy group;

$R_2$ represents hydrogen, halo, a $C_{1-4}$ alkyl group or a $C_{1-4}$ alkoxy group;

$R_3$ represents hydrogen, a $C_{1-4}$ alkoxy group or hydroxy;

n=2 and m=1–3;

$R_5$ represents hydrogen, a $C_{1-4}$ alkyl group or a phenyl $C_{1-4}$ alkyl group (in which the phenyl ring is optionally substituted by one or more of the following: a $C_{1-4}$ alkyl group, a $C_{1-4}$ alkoxy group or halo); and $R_6$ represents a $C_{1-4}$ alkyl group or a phenyl $C_{1-4}$ alkyl group (in which the phenyl ring is optionally substituted by one or more of the following: a $C_{1-4}$ alkyl group, a $C_{1-4}$ alkoxy group or halo);

or $R_5$ and $R_6$ together with the nitrogen atom to which they are attached represent a pyrrolidine ring, a piperidine ring or a morpholine ring.

The preferred values of $R_1$, $R_2$, $R_3$, $R_5$, $R_6$, and m in preferred compounds of formula III are listed below.

Preferably $R_1$ represents hydrogen, chloro, fluoro, methoxy or methyl. More preferably $R_1$ represents hydrogen, chloro, fluoro or methyl. Most preferably $R_1$ represents hydrogen or chloro.

Preferably $R_2$ represents hydrogen or chloro.

Preferably $R_3$ represents hydrogen, hydroxy or methoxy. More preferably $R_3$ represents hydrogen.

Preferably $R_5$ represents hydrogen, methyl, ethyl or propyl and $R_6$ represents methyl, ethyl, propyl or benzyl or $R_5$ and $R_6$ together with the nitrogen atom to which they are attached represent a pyrrolidine ring or a piperidine ring. More preferably, $R_5$ represents methyl and $R_6$ represents methyl or benzyl or $R_5$ and $R_6$ together with the nitrogen atom to which they are attached represent a piperidine ring. Most preferably, $R_5$ and $R_6$ both represent methyl.

Preferably m represents 1, 2 or 3. More preferably m represents 1 or 2. Most preferably m represents 1.

Specific compounds of formula I are:

4-aminomethyl-1-(2-phenoxyethyl)piperidine;
4-aminomethyl-1-[2-(4-chlorophenoxy)ethyl]piperidine;
4-aminomethyl-1-(3-phenoxypropyl)piperidine;
4-aminomethyl-1-[2-(4-methoxyphenoxy)ethyl]piperidine;
4-(dimethylaminomethyl)-1-[2-(4-methylphenoxy)ethyl]piperidine;
1-[2-(3-chlorophenoxy)ethyl]-4-(dimethylaminomethyl)piperidine;
4-(N-benzylaminomethyl)-1-(2-phenoxyethyl)piperidine;
4-(N-benzyl-N-methylaminomethyl)-1-(2-phenoxyethyl)piperidine;
4-(dimethylaminomethyl)-1-(2-phenoxyethyl)piperidine;
1-[2-(4-chlorophenoxy)ethyl]-4-(dimethylaminomethyl)piperidine;
4-(dimethylaminomethyl)-1-[2-(4-fluorophenoxy)ethyl]piperidine;
4-(dimethylaminomethyl)-1-[2-(4-methoxyphenoxy)ethyl]piperidine;
4-(dimethylaminomethyl)-1-(3-phenoxypropyl)piperidine;
4-(2-dimethylaminoethyl)-1-[2-(4-methylphenoxy)ethyl]piperidine;

4-(2-dimethylaminoethyl)-1-[2-(4-fluorophenoxy)ethyl] piperidine;
4-[2-(N-benzyl-N-methylamino)ethyl]-1-(2-phenoxyethyl) piperidine;
1-[2-(3-chlorophenoxy)ethyl]-4-(2-dimethylaminoethyl) piperidine;
1-(2-phenoxyethyl)-4-(2-piperidinoethyl)piperidine;
2-{2-[4-(2-dimethylaminoethyl)piperidino]ethoxy}phenol;
4-(2-dimethylaminoethyl)-1-(2-phenoxyethyl)piperidine;
1-(2-phenoxyethyl)-4-[2-(pyrrolidin-1-yl)ethyl]piperidine;
1-[2-(4-chlorophenoxy)ethyl]-4-(2-dimethylaminoethyl) piperidine;
4-(2-dimethylaminoethyl)-1-[2-(2-methoxyphenoxy)ethyl] piperidine;
4-(2-dimethylaminoethyl)-1-[2-(4-methoxyphenoxy)ethyl] piperidine;
4-(3-dimethylaminopropyl)-1-(2-phenoxyethyl)piperidine;
4-(2-dimethylaminoethyl)-1-(3-phenoxypropyl)piperidine;
4-(2-dimethylaminoethyl)-1-(4-phenoxybutyl)piperidine;
4-[1-(4-chlorophenyl)ethylaminomethyl]-1-(2-phenoxyethyl)piperidine;
4-{2-[1-(4-chlorophenyl)ethylamino]ethyl}-1-(2-phenoxyethyl)piperidine;
4-(diethylaminomethyl)-1-(2-phenoxyethyl)piperidine;
4-(ethylaminomethyl)-1-(2-phenoxyethyl)piperidine;
4-(N-ethyl-N-methylaminomethyl)-1-(2-phenoxyethyl) piperidine;
1-(2-phenoxyethyl)-4-(propylaminomethyl)piperidine;
4-(2-dimethylaminoethylidene)-1-(2-phenoxyethyl) piperidine;
1-(2-phenoxyethyl)-4-[2-(pyrrolidin-1-yl)ethylidene] piperidine;
4-[2-(N-benzyl-N-methylamino)ethylidene]-1-(2-phenoxyethyl)piperidine;
1-[2-(4-chlorophenoxy)ethyl]-4-(2-dimethylaminoethylidene)piperidine;
4-(2-dimethylaminoethylidene)-1-[2-(2-methoxyphenoxy) ethyl]piperidine;
4-(2-dimethylaminoethylidene)-1-[2-(4-methoxyphenoxy) ethyl]piperidine;
1-(2-phenoxyethyl)-3-(pyrrolidin-1-ylmethyl)piperidine;
1-(2-phenoxyethyl)-3-(piperidin-1-yl methyl)piperidine;
(E)-3-(3-dimethylamino-1-propenyl)-1-(2-phenoxyethyl) piperidine;
3-(3-dimethylaminopropyl)-1-(2-phenoxyethyl)piperidine;

and pharmaceutically acceptable salts thereof, in the form of individual enantiomers, racemates or other mixtures of enantiomers.

The compounds of formula I may form organic or inorganic salts, for example, the compounds of formula I may form acid addition salts with inorganic or organic acids, e.g. hydrochloric acid, hydrobromic acid, fumaric acid, tartaric acid, citric acid, sulphuric acid, hydriodic acid, phosphoric acid, maleic acid, acetic acid, succinic acid, benzoic acid, pamoic acid, palmitic acid, dodecanoic acid and acidic amino acids such as glutamic acid. Some compounds of formula I may form base addition salts, for example, with alkali metal hydroxides for example sodium hydroxide, or with aminoacids for example, lysine or arginine or with organic bases, for example meglumine. Certain compounds of formula I may exist in Zwitterionic form. It will be appreciated that all such salts, provided they are pharmaceutically acceptable may be used in therapy in place of the corresponding compounds of formula I. Such salts are prepared by reacting the compound of formula I with a suitable acid or base in a conventional manner. Such salts may also exist in the form of solvates (for example, hydrates).

It will be appreciated by those skilled in the art that certain compounds of formula I contain one or more chiral centres. Certain of the substituents $R_1$, $R_2$, $R_3$, $R_5$ and $R_6$ may also contain at least one chiral centre, for example when $R_1$, $R_2$, $R_3$, $R_5$ and $R_6$ is sec-butyl.

When a compound of formula I, or a salt thereof, contains a single chiral centre it may exist in two enantiomeric forms. The present invention includes individual enantiomers and mixtures of those enantiomers. The enantiomers may be obtained by methods known to those skilled in the art. Such methods typically include resolution via formation of diastereoisomeric salts or complexes which may be separated, for example, by crystallisation; resolution via formation of diastereoisomeric derivatives or complexes which may be separated, for example, by crystallisation, gas-liquid or liquid chromatography; selective reaction of one enantiomer by reaction with an enantiomer-specific reagent, for example, enzymatic esterification, followed by separation of the modified and unmodified enantiomers; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, a further step will subsequently be required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I, or a salt thereof, contains more than one chiral centre it may exist in diastereoisomeric forms. The diastereoisomeric pairs may be separated by methods known to those skilled in the art, for example, chromatography or crystallisation and the individual enantiomers within each pair may be separated as described above. The present invention includes each diastereoisomer of compounds of formula I and mixtures thereof.

Certain compounds of formula I may exist in more than one geometric isomeric form for example when a double bond is present between Y and $C(R^4)$. The present invention includes each geometric isomer and mixtures thereof.

Certain compounds of formula I and their salts may exist in more than one crystal form and the present invention includes each crystal form and mixtures thereof. Certain compounds of formula I may also exist in the form of solvates, for example hydrates, and the present invention includes each solvate and mixtures thereof.

The present invention also provides pharmaceutical compositions comprising a therapeutically effective amount of a compound of formula I or a pharmaceutically acceptable salt thereof (including the three excluded compounds) together with a pharmaceutically acceptable diluent or carrier. Such pharmaceutical compositions may be used in the treatment of inflammatory and/or allergic diseases.

As used hereinafter, the term "active compound" denotes a compound of formula I or a pharmaceutically acceptable salt thereof. In therapeutic use the active compound may be administered orally, rectally, parenterally, topically, ocularly, aurally, nasally, intravaginally or to the buccal cavity, to give a local and/or a systemic effect. The active compounds may be administered in a prophylactic manner. Thus the therapeutic compositions of the present invention may take the form of any of the known pharmaceutical compositions for such methods of administration. The compositions may be formulated in a manner known to those skilled in the art so as to give a controlled release, for example rapid release or sustained release, of the compounds of the present invention. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, granules, syrups and aqueous or oily suspensions. The excipients used in the preparation of these compositions are the excipients known in the pharmacists' art.

Tablets may be prepared from a mixture of the active compound with fillers, for example, lactose or calcium phosphate, disintegrating agents, for example maize starch, lubricating agents, for example magnesium stearate, binders for example microcrystalline cellulose or polyvinyl pyrrolidone and other optional ingredients known in the art to permit tableting the mixture by known methods. The tablets may, if desired, be coated using known methods and excipients which may include enteric coating using for example hydroxypropylmethyl-cellulose phthalate.

The tablets may be formulated in a manner known to those skilled in the art so as to give a sustained release of the compounds of the present invention Such tablets may if desired be provided with enteric coatings by known methods, for example by the use of cellulose acetate phthalate.

Similarly capsules, for example hard or soft gelatin capsules containing the active compound with or without added excipients, may be prepared by known methods and, if desired, provided with enteric coatings in a known manner. The contents of the capsule may be formulated using known methods to give sustained release of the active compound. Enteric coated compositions of the invention may be advantageous, depending on the nature of the active compound. The tablets and capsules may conveniently each contain 1–1000 mg (for example 10 mg, 50 mg, 100 mg, 200 mg, 400 mg, 600 mg or 800 mg) of the active compound. Other compositions for oral administration include, for example, aqueous suspensions containing the compound of formula I in an aqueous medium in the presence of a non-toxic suspending agent such as sodium carboxymethylcellulose, and oily suspensions containing a compound of the present invention in a suitable vegetable oil, for example sunflower oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example suppositories with hard fat, semi-synthetic glycerides or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the active compound is dispersed so that it is held in contact with the skin in order to administer the active compound transdermally. Alternatively the active compound may be dispersed in a cream, gel or ointment base or applied in the form of a spray.

Compositions of the invention suitable for inhalation via the mouth and/or the nose are the known pharmaceutical forms for such administration, for example aerosols, nebulised solutions or powders. Metered dose systems, known to those skilled in the art, may be used.

Compositions suitable for application to the buccal cavity include slow dissolving tablets, troches, chewing gum, gels, pastes, powders, mouthwashes or rinses.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be a) liquid such as an oily solution or suspension of the compound to be infused for example in the form of a very sparingly water-soluble derivative such as a dodecanoate salt or b) solid in the form of an implanted support for example a synthetic resin or waxy material for the compound to be infused. The support may be a single body containing all the compound or a series of several bodies each containing part of the compound to be delivered.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example:

a) an analgesic (e.g. in treatment of rheumatoid arthritis),
b) a $\beta 2$ agonist (e.g. in treatment of asthma) and c) a non-sedating antihistamine (e.g. in treatment of other allergic conditions).

The pharmaceutical compositions containing a therapeutically effective amount of a compound of formula I may be used to treat inflammatory and/or allergic conditions in human beings. In such treatment the amount of the compound of formula I administered per day is in the range 0.1 to 3000 mg. Specific compounds which may be incorporated into the compositions of this invention are the novel compounds disclosed above.

The therapeutic activity of compounds of formula I has been demonstrated by means of tests on standard laboratory animals. Such tests include, for example, the oral administration of the compounds to rats in which an inflammatory condition is induced. Thus, compounds of formula I are useful for the treatment of inflammatory conditions in mammals. Whilst the precise amount of active compound administered will depend on a number of factors, for example the age of the patient, the severity of the condition and the past medical history and always lies within the sound discretion of the administering physician, a suitable dose for enteral administration to mammals, including humans, is generally within the range 0.01–80 mg/kg/day, more usually 0.2–40 mg/kg/day given in single or divided doses. For parenteral administration, a suitable dose is generally within the range 0.01–80 mg/kg/day, more usually 0.2–40 mg/kg/day given in single or divided doses or by continuous infusion. Oral administration is preferred.

Compounds of formula I and pharmaceutically acceptable salts thereof (including the three excluded compounds) are indicated for use as medicaments particularly in the treatment of inflammatory and/or allergic conditions for example musculoskeletal disorders for example: rheumatoid arthritis, osteo-arthritis, systemic lupus erythematosus, muscle trauma, gout, ankylosing spondylitis, tendonitis and bursitis; respiratory disorders for example: asthma and rhinitis; gastrointestinal disorders for example: gastritis, Crohn's disease, ulcerative colitis and other inflammatory diseases of the bowel; diseases of the oral cavity for example: periodontitis and gingivitis; cutaneous disorders for example: psoriasis, urticaria, allergic skin diseases, burns, ocular inflammation and iritis; or Alzheimer's disease. Compounds of formula I and salts thereof may also be useful as analgesics and/or anti-pyretic agents.

Accordingly, in another aspect, the present invention also includes a method of treating inflammatory and/or allergic conditions comprising the administration of a therapeutically effective amount of a compound of formula I or a pharmaceutically acceptable salt thereof (including the three excluded compounds) to a mammal in need thereof.

While the precise mechanism of action of the compounds of formula I is unknown at present, it is believed that the pharmacological effects arise from the ability of these compounds to inhibit the release of arachidonic acid from phospholipids. Consequently, in a preferred aspect, the present invention provides a method of treating inflammatory and/or allergic conditions comprising the administration of a therapeutically effective amount of an arachidonic acid release inhibitor of formula I or a pharmaceutically acceptable salt thereof (including the three excluded compounds) to a mammal in need thereof.

In yet another aspect, the present invention provides the use of a compound of formula I or a pharmaceutically acceptable salt thereof (including the three excluded compounds) in the manufacture of a medicament for use in the treatment of an inflammatory and/or allergic condition.

The compounds of formula I may also be indicated for use as immunomodulatory agents, generally as immunosuppressants, but some compounds, in certain disease states, may exhibit immunostimulant activity. The compounds according to the invention may be useful in the treatment of diseases resulting from an aberrant immune reaction. Thus the pharmaceutical compositions containing a therapeutically effective amount of a compound of formula I or a pharmaceutically acceptable salt thereof (including the three excluded compounds) may be used to treat diseases with an immunological association for example tissue rejection, such as kidney rejection; autoimmune diseases, such as thyroiditis and type 1 diabetes; cutaneous disorders, such as contact sensitivity, eczema and psoriasis; neoplasia, such as melanoma; and HIV infection.

In such treatment the amount of the compound of formula I administered per day will be such as to give a therapeutic effect and is generally in the range 0.1 to 2000 mg, preferably 1 to 500 mg.

Accordingly, in another aspect, the present invention also includes a method of treating diseases with an immunological association, comprising the administration of a therapeutically effective amount of a compound of formula I or a pharmaceutically acceptable salt thereof (including the three excluded compounds) to a mammal in need thereof.

In yet another aspect, the present invention provides the use of a compound of formula I or a pharmaceutically acceptable salt thereof (including the three excluded compounds) in the manufacture of a medicament for use in the treatment of diseases with an immunological association.

The therapeutic activity of compounds falling within formula I may be demonstrated by means of in vitro and in vivo tests. Such tests include, for example, the in vitro mixed lymphocyte reaction and an in vivo rat Graft versus Host (GvH) test. Thus, compounds of formula I may be useful as immunomodulatory agents.

The compounds of formula I and pharmaceutically acceptable salts thereof may also be indicated for use as disease-modifying antirheumatic agents. Such activity may be demonstrated by means of in vivo tests such as the antigen induced mouse arthritis test as described in WO 93/13097.

Processes for the preparation of compounds of formula I will now be described. These processes form a further aspect of the present invention. Unless otherwise stated the processes are carried out at atmospheric pressure.

Compounds of formula I may be prepared by reacting a compound of formula IV

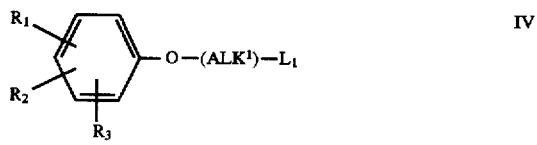

in which $R_1$, $R_2$, $R_3$ and $ALK^1$ are as previously defined and $L_1$ represents a leaving group, for example halo or tosyl, with a compound of formula V

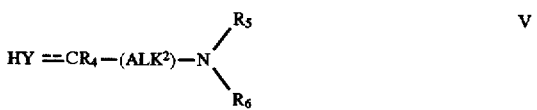

in which Y, $R_4$, $ALK^2$, $R_5$ and $R_6$ are as previously defined, optionally in the presence of an inert organic liquid which is preferably a solvent for the reactants, e.g. N,N-dimethylformamide, at a temperature in the range from 0° C. up to the boiling point of the inert organic liquid, e.g. 0°–250° C., preferably by heating at a temperature in the range 20°–150° C., optionally in the presence of a base e.g. triethylamine.

Compounds of formula I in which $R_5$ represents a group other than hydrogen may be prepared by reacting a compound of formula VI

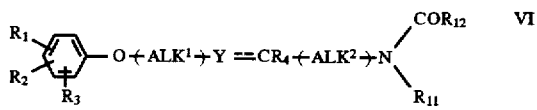

in which $R_1$, $R_2$, $R_3$, $ALK^1Y$, $R_4$ and $ALK^2$ are as initially defined and $R_{12}CO$ represents a group which on reduction yields a group $R_5$ of formula $-CH_2R_{12}$ and $R_{11}$ represents $R_6$ (or $R_{12}CO$ to give compounds in which $R_5$ and $R_6$ are identical), with a reducing agent, for example lithium aluminium hydride, preferably in the presence of an inert organic liquid which is preferably a solvent for the compound of formula VI, for example tetrahydrofuran, at a temperature in the range from −50° C. up to the boiling point of the inert organic liquid e.g. −50° to 200° C., preferably at a temperature in the range −10° to 150° C.

Compounds of formula I in which $R_5$ represents hydrogen may be prepared by reacting a compound of formula VII

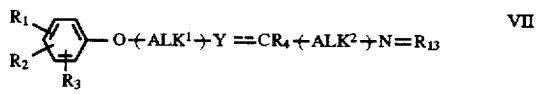

in which $R_1$, $R_2$, $R_3$, $ALK^1Y$, $R_4$ and $ALK^2$ are as initially defined and $-N=R_{13}$ represents a group which on reduction yields $-NHR_6$, for example benzylimino, with a reducing agent, for example sodium borohydride, preferably in the presence of an organic liquid which is a solvent for the compound of formula VII, for example an alcohol e.g. ethanol, at a temperature in the range 0°–200° C., preferably by heating at a temperature in the range 20°–150° C.

Compounds of formula I in which $R_5$ represents hydrogen may be prepared by deprotecting a compound of formula VIII

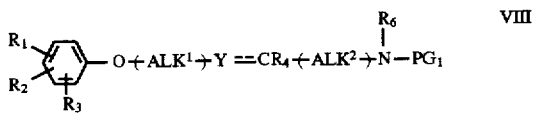

in which $R_1$, $R_2$, $R_3$, $ALK^1$, Y, $R_4$, $R_6$ and $ALK^2$ are as initially defined and $PG_1$ represents an amine protecting group for example benzoyl e.g. by hydrolysis. Suitable methods for protecting and deprotecting amines may be found in the textbook "Protective Groups in Organic Synthesis" by T. W. Greene, John Wiley and Sons, 1981.

Compounds of formula I in which ($CR_4$) is connected to Y by a double bond may be prepared by reacting a compound of formula IX

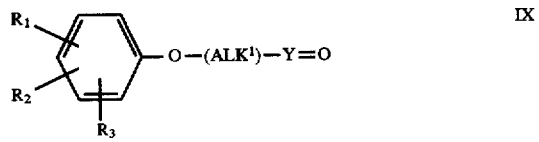

in which $R_1$, $R_2$, $R_3$, $ALK^1$ and Y are as initially defined, with a Wittig reagent, for example (a) a compound of formula Xa

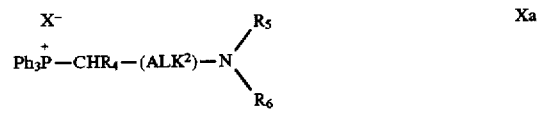

in which $ALK^2$, $R_4$, $R_5$ and $R_6$ are as initially defined and X represents halo, or (b) a compound of formula Xb

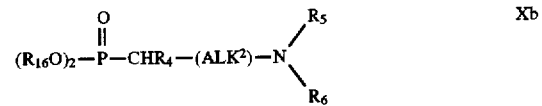

in which $ALK^2$, $R_4$, $R_5$ and $R_6$ are as initially defined and $R_{16}$ represents an alkyl group, in which Xa or Xb has been pretreated with a base, e.g. n-butyllithium, in an inert organic liquid e.g. tetrahydrofuran, and the mixture combined in an inert organic liquid e.g. tetrahydrofuran, at a temperature in the range from 0° C. up to the boiling point of the inert organic liquid, e.g. 0°–200° C., preferably by heating at a temperature in the range 20°–150° C.

Compounds of formula I may be prepared by reducing compounds of formula XI

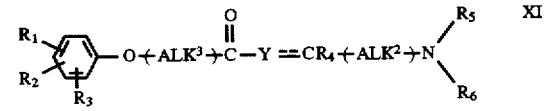

in which $R_1$, $R_2$, $R_3$, Y, $R_4$, $ALK^2$, $R_5$ and $R_6$ are as initially defined and —$ALK^3$—CO— represents a group which on reduction yields a group of formula —$ALK^1$—, for example using borane, in an inert organic liquid which is preferably a solvent for XI, for example tetrahydrofuran, at a temperature in the range from 0° C. up to the boiling point of the inert organic liquid e.g. 0°–200° C., preferably by heating at a temperature in the range 20°–150° C.

Compounds of formula I in which $R_5$ and $R_6$ represent hydrogen may be prepared by hydrolysing compounds of formula XII

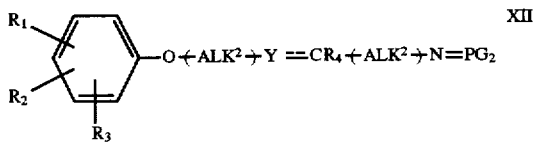

in which $R_1$, $R_2$, $R_3$, $ALK^1$, $R_4$ and $ALK^2$ are as initially defined and $PG_2$ represents an amine protecting group, for example dimethylaminomethylene or 4-chloro-α-methylbenzylidene, preferably in the presence of a base, e.g. aqueous ammonia, or an acid, e.g. a mineral or an organic acid, e.g. hydrochloric acid or acetic acid, at a temperature in the range 0°–250° C., preferably by heating at a temperature in the range of 20°–100° C.

Compounds of formula I may be prepared by reducing a compound of formula XIII

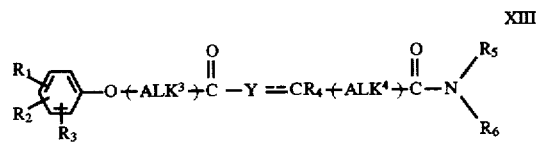

in which $R_1$, $R_2$, $R^3$, Y, $R_4$, $R_5$ and $R_6$ are as initially defined and —($ALK^3$)—CO— and ($ALK^4$)—CO— represent groups which on reduction give $ALK^1$ and $ALK^2$ respectively, for example using borane, in an inert organic liquid which is preferably a solvent for the compound of formula XIII, for example tetrahydrofuran, at a temperature in the range from 0° C. up to the boiling point of the inert organic liquid, e.g. 0°–200° C., preferably by heating at a temperature in the range 20°–150° C. It will be appreciated by those skilled in the art that if an olefinic double bond is present in XIII that this bond may also be reduced.

Compounds of formula I in which —$CR_4$— represents methylene, $ALK^2$ is absent and $R_5$ and $R_6$ represent hydrogen may be prepared by reacting a compound of formula XIV

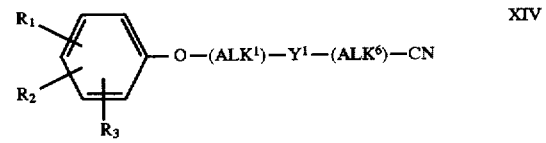

in which $R_1$, $R_2$, $R_3$, $ALK^1$ are as initially defined, $ALK^6$ is absent and $Y^1$ represents a piperidine ring, or a pyridinium ring having a halide counter ion, with a reducing agent, for example lithium aluminium hydride or hydrogen in the presence of a catalyst, e.g. palladium on charcoal, in an inert organic liquid which is preferably a solvent for the compound of formula XIV, for example tetrahydrofuran, at a temperature in the range from 0° C. up to the boiling point of the inert organic liquid, e.g. 0°–200° C., preferably by heating at a temperature in the range 20°–150° C.

Compounds of formula I in which the broken line is absent, the free valency on Y is taken up by hydrogen, the free valency on $CR_4$ is taken up by hydrogen or a $C_{1-4}$ alkyl group, $R_5$ and $R_6$ each represent hydrogen and $ALK^2$ represents a $C_{1-4}$ alkylene chain may be prepared by reacting a compound of formula XIV

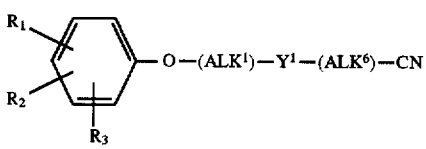

XIV in which —(ALK$^6$)—CN represents a group which on reduction gives —CH(R$_4$)—(ALK$^2$)—NH$_2$ and Y$^1$ represents a piperidine ring, or a pyridinium ring having a halide counter ion, with a reducing agent, for example lithium aluminium hydride or hydrogen in the presence of a catalyst, erg. palladium on charcoal, in an inert organic liquid which is preferably a solvent for the compound of formula XIV, for example tetrahydrofuran, at a temperature in the range from 0° C. up to the boiling point of the inert organic liquid, e.g. 0°–200° C., preferably by heating at a temperature in the range 20°–150° C.

Compounds of formula I may be prepared by reacting a compound of formula XV

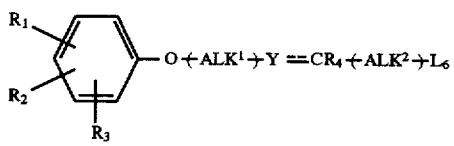

XV in which R$_1$, R$_2$, R$_3$, ALK$^1$, Y, R$_4$ and ALK$^2$ are as initially defined and L$_6$ represents a leaving group, for example halo, with a compound of formula XXX

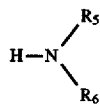

XXX in which R$_5$ and R$_6$ are as initially defined, optionally in the presence of an inert organic liquid which is preferably a solvent for the reactants, for example N,N-dimethylformamide or tetrahydrofuran, at a temperature in the range from 0° C. up to the boiling point of the inert organic liquid e.g. 0°–250° C., preferably by heating at a temperature in the range 20°–150° C.

Compounds of formula I may be prepared by reacting a compound of formula XVI

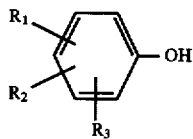

XVI in which R$_1$, R$_2$ and R$_3$ are as initially defined with a compound of formula XVIII

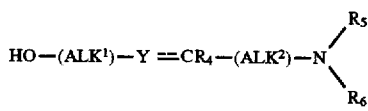

XVIII in which ALK$^1$, Y, R$_4$, ALK$^2$, R$_5$ and R$_6$ are as initially defined, in the presence of a dialkyl azodicarboxylate, for example diethyl azodicarboxylate, and a phosphorus (III) reagent for example, triphenylphosphine, optionally in the presence of an inert organic liquid which is preferably a solvent, for example tetrahydrofuran, at a temperature in the range from 0° C. up to the boiling point of the inert organic liquid, for example 0°–250° C., preferably by heating at a temperature in the range 0°–150° C.

Compounds of formula I in which R$_5$ and R$_6$ each represent hydrogen and ALK$^2$ is absent may be prepared by reacting compounds of formula XL

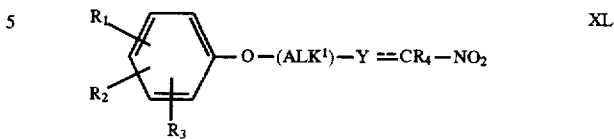

XL in which R$_1$, R$_2$, R$_3$, ALK$^1$, Y and R$_4$ are as initially defined with a reducing agent, for example iron and ammonium chloride solution or hydrogen in the presence of a catalyst. It will be appreciated by those skilled in the art that if an olefinic double bond is present in XL that this bond may also be reduced or left intact, as desired, by the choice of reducing agent.

Compounds of formula I may be prepared by reacting a compound of formula V

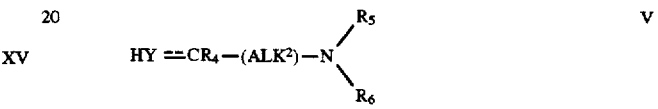

V in which Y, R$_4$, ALK$^2$, R$_5$ and R$_6$ are as initially defined with a compound of formula XLI

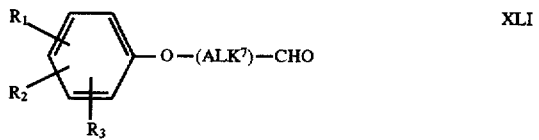

XLI in which R$_1$, R$_2$ and R$_3$ are as initially defined and —(ALK$^7$)—CHO represents a group which on reaction and reduction yields a group of formula ALK$^1$, optionally in the presence of an inert organic liquid which is preferably a solvent for V and XLI, for example toluene, at a temperature in the range from 0° C. up to the boiling point of the inert organic liquid e.g. 0°–250° C., preferably by heating at a temperature in the range 20°–150° C., followed by reaction of the product with a reducing agent, for example sodium borohydride or sodium cyanoborohydride, optionally in the presence of an inert organic liquid which is preferably a solvent for the reactants, e.g. ethanol, at a temperature in the range 0°–250° C., preferably by heating at a temperature in the range 20°–150° C.

Compounds of formula I may be prepared by reacting a compound of formula XVI with a compound of formula XLII

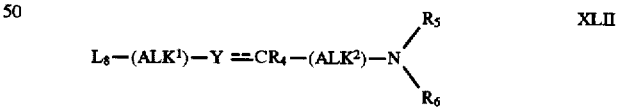

XLII in which ALK$^1$, Y, R$_4$, ALK$^2$, R$_5$ and R$_6$ are as initially defined and L$_8$ represents a leaving group, for example halo or tosyl, optionally in the presence of an inert organic liquid, which is preferably a solvent for the reactants, for example N,N-dimethylformamide or an alcohol, at a temperature in the range 0°–250° C., preferably by heating at a temperature in the range 20°–150° C., optionally in the presence of a base, for example sodium hydroxide.

Compounds of formula IV may be prepared by methods known to those skilled in the art for example by reacting a compound of formula XVI with a compound of formula XVII

XVII in which ALK¹ is as initially defined and $L_1$ and $L_2$ independently represent a leaving group which may be the same or different provided that $L_2$ is more labile than $L_1$, for example halo or tosyl.

Compounds of formula V may be prepared by hydrolysing compounds of formula XIX

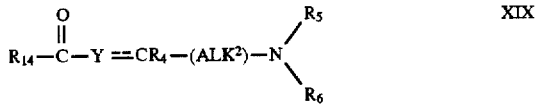

in which Y, $R_4$, $ALK^2$, $R_5$ and $R_6$ are as initially defined and $R_{14}CO$ represents a hydrolysable acyl group, for example acetyl or benzoyl, for example by reaction with dilute hydrochloric acid at a temperature in the range 0°–250° C., preferably by heating at a temperature in the range 20°–150° C., optionally followed by basification.

Compounds of formula VI may be prepared by reacting a compound of formula XX

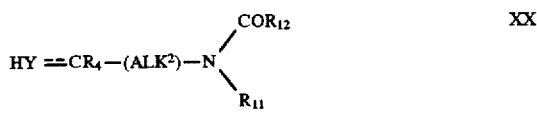

in which Y, $R_4$, $ALK^2$, $R_{11}$ and $R_{12}CO$ are as initially defined, with a compound of formula IV in an analogous manner to the preparation of a compound of formula I from a compound of formula IV and a compound of formula V.

Compounds of formula VI may also be prepared by reacting a compound of formula I in which $R_5$ and/or $R_6$ represents hydrogen with a compound of formula XXI

in which $R_{12}CO$ is as initially defined and $L_3$ represents a leaving group, for example halo, by methods known to those skilled in the art.

Compounds of formula VII may be prepared by reacting a compound of formula XXII

in which Y, $R_4$, $ALK^2$ and $-N=R_{13}$ are as initially defined, with a compound of formula IV in an analogous manner to the preparation of a compound of formula I from a compound of formula IV and a compound of formula V.

Compounds of formula VIII may be prepared in a similar manner to compounds of formula VII by reacting a compound of formula XXIII

in which Y, $R_4$, $ALK^2$, $PG_1$ and $R_6$ are as initially defined with a compound of formula IV.

Compounds of formula IX may be prepared by reacting a compound of formula XXIV

in which Y is as initially defined, with a compound of formula IV optionally in the presence of an inert organic liquid which is preferably a solvent for the reactants, at a temperature in the range 0°–250° C. optionally in the presence of a base, for example triethylamine or sodium bicarbonate.

Compounds of formula Xa and Xb may be prepared by methods known to those skilled in the art for example Xa may be prepared by reacting triphenylphosphine with a compound of formula XXV

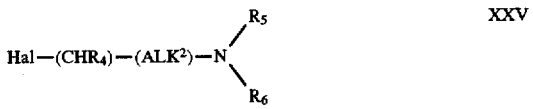

in which $R_4$, $ALK^2$, $R_5$ and $R_6$ are as initially defined.

Compounds of formula XI may be prepared by reacting a compound of formula XXVI

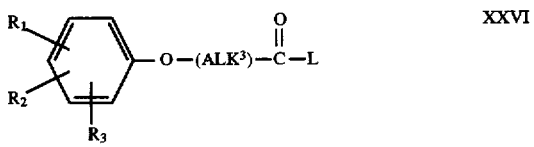

in which $R_1$, $R_2$, $R_3$ and $ALK^3$ are as initially defined and L represents a leaving group, for example halo, with a compound of formula V for example in the presence of a base, e.g. triethylamine, in an inert organic liquid, e.g. dichloromethane at a temperature in the range from 0° C. up to the boiling point of the inert organic liquid, e.g. 0°–200° C., preferably by heating at a temperature in the range 20°–150° C.

Compounds of formula XI may also be prepared by reacting a compound of formula XXVII

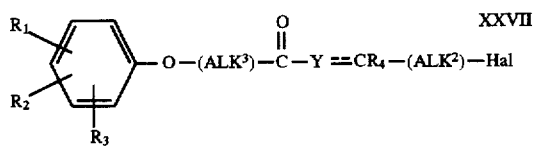

in which $R_1$, $R_2$, $R_3$, $ALK^3$, Y, $R_4$ and $ALK^2$ are as initially defined and Hal represents chloro, bromo or iodo with a compound of formula XXX

in which $R_5$ and $R_6$ are as initially defined, for example in an inert organic liquid, e.g. tetrahydrofuran, at a temperature in the range 0°–150° C. in the presence of a base, for example triethylamine, preferably by heating at a temperature in the range 20°–150° C. It will be appreciated by those skilled in the art that this reaction may give rise to quaternary salt by-products from which the desired product may be separated by known techniques, e.g. distillation.

Compounds of formula XII may be prepared by reacting a compound of formula XXXIX

in which $R_4$, $ALK^2$ and $PG_2$ are as initially defined with a compound of IV for example in the presence of a base, e.g. triethylamine in an inert organic liquid, e.g. dichloromethane or toluene, at a temperature in the range from 0° C. up to the boiling point of the inert organic liquid, e.g. 0°–200° C., preferably by heating at a temperature in the range 20°–150° C.

Compounds of formula XIII may be prepared by reacting a compound of formula XXIX

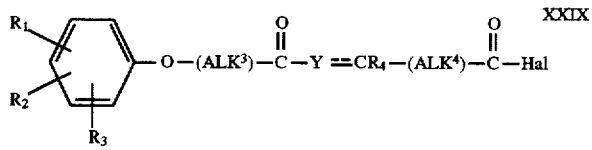

in which $R_1$, $R_2$, $R_3$, $ALK^3$, Y, $R_4$, $ALK^4$ and Hal are as initially defined with a compound of formula XXX by methods known to those skilled in the art.

Compounds of formula XIV in which $Y^1$ represents piperidine may be prepared by reacting a compound of formula XXVIII

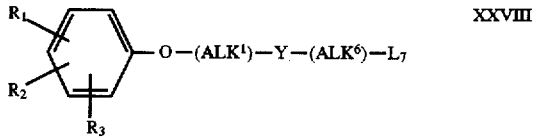

in which $R_1$, $R_2$, $R_3$, $ALK^1$, Y and $ALK^6$ are as initially defined and $L_7$ represents a leaving group, for example halo or tosyl, with a cyanide salt for example potassium cyanide, by methods known to those skilled in the art.

Compounds of formula XIV in which $Y^1$ represents a piperidine ring may also be prepared by reducing compounds of formula XIV, in which $Y^1$ represents a pyridinium ring with a halide counter ion, by methods known to those skilled in the art for example by reacting with sodium borohydride in a solvent e.g. ethanol.

Compounds of formula XIV in which $Y^1$ represents a pyridinium ring having a halide counter ion may be prepared by alkylation of an appropriate cyanopyridine or cyanoalkylpyridine, for example with a compound of formula IV, by methods known to those skilled in the art.

Compounds of formula XV may be prepared from compounds of formula XXXVIII

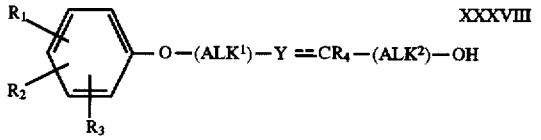

in which $R_1$, $R_2$, $R_3$, $ALK^1$, Y, $R_4$ and $ALK^2$ are as initially defined by methods known to those skilled in the art.

Compounds of formulae XVI, XVII and XXI are commercially available or may be prepared by methods known to those skilled in the art.

Compounds of formula XVIII may be prepared from compounds of formula V by methods known to those skilled in the art for example by hydroxyalkylation.

Compounds of formula XIX may be prepared by reacting a compound of formula XXXI

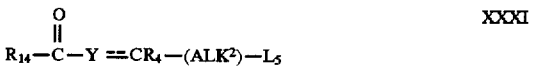

in which $R_{14}$, Y, $R_4$ and $ALK^2$ are as initially defined and $L_5$ represents a leaving group, for example halo, with a compound of formula XXX in an analogous manner to the preparation of a compound of formula XI from a compound of formula XXVII and a compound of formula XXX.

Compounds of formula XX may be prepared by acylating a compound of formula XXXII

in which Y, $R_4$, $ALK^2$ and $R_6$ are as initially defined, or by diacylating a compound of formula XXXII in which $R_6$ represents hydrogen, by methods known to those skilled in the art.

Compounds of formula XXII may be prepared from compounds of formula XXXII by methods known to those skilled in the art, for example by reacting a compound of formula XXXII, in which $R_6$ is hydrogen, with an aldehyde of formula $HR_{13}$=O.

Compounds of formula XXIII may be prepared by protecting compounds of formula XXXII

in which Y, $R_4$, $ALK^2$ and $R_6$ are as initially defined by methods known to those skilled in the art.

Compounds of formula XXIV, XXV, XXVI, XXX and XLI are commercially available or may be prepared by methods known to those skilled in the art.

Compounds of formula XXVII may be prepared by reacting a compound of formula XXXIII

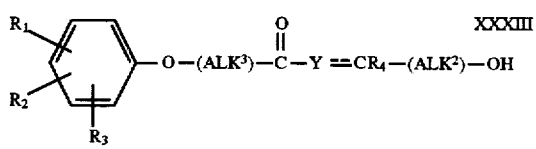

in which $R_1$, $R_2$, $R_3$, $ALK^3$, Y, $R_4$ and $ALK^2$ are as initially defined, with a halogenating agent, e.g. thionyl chloride, at a temperature in the range 0°–200° C. in the presence or absence of an inert organic liquid, e.g. chloroform, preferably by heating at a temperature in the range 20°–150° C.

Compounds of formula XXVIII may be prepared in an analogous manner to compounds of formula XV.

Compounds of formula XXIX may be prepared by halogenating a compound of formula XXXIV

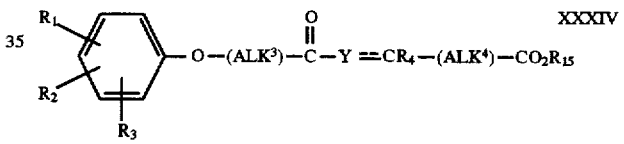

in which $R_1$, $R_2$, $R_3$, $ALK_3$, Y, $R_4$ and $ALK^4$ are as initially defined and $R_{15}$ represents hydrogen for example by reaction with thionyl chloride at a temperature in the range 0°–200° C. in the presence or the absence of an inert organic liquid, e.g. chloroform, preferably by heating at a temperature in the range of 20°–150° C.

Compounds of formula XXXI may be prepared from compounds of formula XXXV

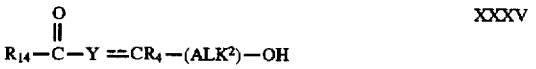

in which $R_{14}$, Y, $R_4$ and $ALK^2$ are as initially defined, for example, by reaction with the halogenating agent, for example thionyl chloride at a temperature in the range 0°–200° C. in the presence or the absence of an inert organic liquid, e.g. chloroform, preferably by heating at a temperature in the range of 20°–100° C.

Compounds of formula XXXII may be prepared by methods analogous to those described for the preparation of compounds of formula V.

Compounds of formula XXXIII may be prepared by reacting a compound of formula XXXVI

in which Y, $R_4$ and $ALK^2$ are as initially defined, with a compound of formula XXVI for example, by reaction in the presence of a base, e.g. triethylamine, in an inert organic liquid, e.g. dichloromethane, at a temperature in the range from 0° C. up to the boiling point of the inert organic liquid, e.g. 0°–200° C., preferably by heating in the range 20°–150° C.

Compounds of formula XXXIV may be prepared by reacting a compound of formula XXXVII

$HY\!-\!CR_4\!-\!(ALK^4)\!-\!CO_2R_{15}$  XXXVII in which Y, $R_4$ and $ALK^4$ are as initially defined and $R_{15}$ represents a $C_{1-4}$ alkyl group with a compound of formula XXVI by reaction in the presence of a base, e.g. triethylamine, in an inert organic liquid, e.g. methylene chloride, at a temperature in the range of 0° C. up to the boiling point of the inert organic liquid, e.g. 0°–200° C., preferably by heating to a temperature in the range 20°–150° C. to form a compound of formula XXXIV in which $R_{15}$ represents a $C_{1-4}$ alkyl group and then hydrolysing by reaction with sodium hydroxide in an aqueous non-alcoholic solvent to give a compound of formula XXXIV in which $R_{15}$ represents hydrogen.

Compounds of formula XXXV may be prepared by acylating compounds of formula XXXVI by methods known to those skilled in the art for example by reacting with an acylating agent optionally in the presence of a base, e.g. triethylamine, and then reacting with base at a temperature in the range 0°–100° C. to cleave any O-acylated material.

Compounds of formula XXXVI and XXXVII are commercially available or may be prepared by methods known to those skilled in the art.

Compounds of formula XXXVIII may be prepared by reaction of a compound of formula XXXVI with a compound of formula IV by methods known to those skilled in the art.

Compounds of formula XXXIX may be prepared by protecting compounds of formula HY$-\!CR_4\!-\!(ALK^2)\!-\!NH_2$ (which may be prepared by methods analogous to those described for the preparation of compounds of formula V) by methods known to those skilled in the art.

Compounds of formula XL may be prepared by methods known to those skilled in the art for example by reacting a compound of formula IX with a compound of formula $H_2C(R_4)\!-\!NO_2$, for example using the Knoevenagel condensation.

Compounds of formula XLII may be prepared by methods known to those skilled in the art, for example from compounds of formula XVIII.

It will be appreciated by those skilled in the art that the substituents specified for $R_1$, $R_2$ and $R_3$ may be interconverted by methods known to those skilled in the art. Also certain compounds of formula I may be converted into other compounds of formula I as indicated below.

Compounds of formula I in which $R_5$ and/or $R_6$ represents a group other than hydrogen may be prepared by alkylating a compound of formula I in which $R_6$ and/or $R_5$, respectively, represents hydrogen either a) directly using an alkylating agent of formula $R_5L_3$ or $R_6L_3$ in which $L_3$ represents a leaving group for example halo in the presence of an organic liquid which is preferably a solvent for the reactants at a temperature in the range 0°–150° C. optionally in the presence of a base or b) by reductive alkylation, for example using formaldehyde and formic acid, at a temperature in the range 0°–200° C., preferably by heating at a temperature in the range 20°–150° C., optionally in the presence of an inert organic liquid, which is preferably a solvent for the reactants.

Compounds of formula I in which --- represents a single bond may be prepared by hydrogenating a compound of formula I in which --- represents a double bond, for example by reaction with hydrogen in the presence of a catalyst e.g. palladium on charcoal, in the presence of an inert organic liquid, which is preferably a solvent for the starting compound of formula I, for example an alcohol at a temperature in the range 0°–250° C. preferably 15°–100° C., preferably at a pressure of 1 atmosphere.

It will be appreciated by those skilled in the art that alkylation reactions may give rise to quaternary salt by-products from which the desired product may be separated by known techniques for example distillation.

It will be appreciated by those skilled in the art that in cases where a substituent is identical with, or similar to, a functional group which is being modified in one of the above processes that these substituents will require protection before the process is undertaken, followed by deprotection after the process. Otherwise competing side-reactions will occur. Alternatively, another of the processes described above, in which the substituent does not interfere, may be used.

Compounds of formula II and III may be prepared by processes analogous to those described for the preparation of compounds of formula I.

The compounds of formula I are antiinflammatory agents and may show therapeutic activity at a dose of 200 mg/kg or lower in standard laboratory animals. The therapeutic activity of compounds of formula I has been demonstrated by Test A and one or more of Tests B, C and D.

Test A was carried out in the following way:

Inhibition of Arachidonic Acid Release from Zymosan Stimulated Macrophages

Female MF1 mice (weighing 20 to 25 g) were killed using a rising concentration of $CO_2$. The mice were laid on their backs and the abdomens wiped with 70% alcohol. The skin was pulled back, exposing the peritoneal wall. Medium A (5 ml) (see below) was injected into the peritoneal cavity of each mouse followed by approximately 1 ml of air using a 20 ml syringe and a 21G×40 mm needle in order to form a suspension of macrophage cells. The medium and cells were then removed using a 19G×40 mm needle. The resulting suspension was returned to a sterile beaker kept on ice. The extracts from all the mice were pooled and this pooled cell suspension was counted using a Coulter counter and adjusted to a final cell count of $1$–$1.3\times10^6$ cells/ml prior to labelling with [$^3$H]-arachidonic acid. Typically five mice provided sufficient cells for each multiwell plate.

Sufficient [$^3$H]-arachidonic acid in ethanol to give a final concentration of 1.6 μCi/ml (equivalent to 40 μCi/plate) was blown to dryness under nitrogen. The arachidonic acid was then resuspended in 1 or 2 ml of the cell suspension which was then mixed with the remainder of the cell suspension in a centrifuge bottle. The labelled cell suspension was then plated out into sterile plastic 96 flat-bottomed well plates (250 μl per well) and incubated overnight at 37° C. in a moist atmosphere of 5% $CO_2$, 95% air.

The following day, non-adherent cells were removed by washing 3 times with sterile phosphate buffered saline (PBS). The adherent peritoneal macrophages were then cultured for a further 24 hours in the presence or absence of drugs, in medium B (see below) at 37° in a 5% $CO_2$ atmosphere in order to measure the effects of drugs on the spontaneous release of arachidonic acid in the absence of stimulus. After this incubation, supernatants were removed to give medium 1 and stored in sealed multi-well plates at 4°

C. prior to scintillation counting. Drugs which potentiated spontaneous release of arachidonic acid (125% of controls) were deemed to be toxic at the concentration at which this phenomenon occurred. The supernatants were replaced by fresh medium C containing fresh drug and a stimulus. Three drugs were tested at six concentrations (100, 50, 20, 10, 5 and 1 µM) in replicates of four on each plate. The other wells contained controls consisting of a positive control (e.g. dexamethasone), medium (B) only and medium C only.

Incubation was then continued for a further 5 hours, whereupon the supernatants were collected to give medium 2 and the adherent cells washed with PBS. The cells were then lysed with 100 µl of 0.1% TRITON® X100 in a 0.1% solution of bovine serum albumin in 0.9% saline and mechanically disrupted to give cell lysates. These supernatants (medium 2) and cell lysates (Cells) were also stored in sealed multi-well plates at 4° C. prior to scintillation counting. 200 µl aliquots of media, or 100 µl aliquots of cells were counted using 2 ml of OPTIPHASE "HIGH SAFE" (Trademark of LKB) as scintillant.

Calculation of results

The percentage of arachidonic acid released was calculated using the mean values for each group of 4 wells in the following equation.

$$\% \text{ Release} = \frac{\text{cpm in medium 2}}{\text{cpm in medium 2} + \text{cpm in cell lysate}} \times 100$$

cpm=counts per minute

The value for the arachidonic acid release in the absence of stimulus (spontaneous, cpm of medium 2) from cells which had been exposed to neither stimulus nor drug was subtracted from all equivalent values (cpm media 2, stimulated with or without drug) to give the net stimulated release. The percentage inhibition of arachidonic acid release caused by a drug may then be calculated using the following equation.

$$\% \text{ Inhibition} = 100 - \frac{\text{net stimulated release in presence of drug} \times 100}{\text{net stimulated release in absence of drug}}$$

Compounds of formula I were tested at six concentrations (100, 50, 20, 10, 5 and 1 µM) and $IC_{50}$ values calculated. Compounds with $IC_{50}$ values <100 µM are considered to be active. Advantageous compounds have an $IC_{50}$ value <50 µM.

Medium A (for peritoneal lavage)

To a sterile 100 ml measuring cylinder was added: 40 ml TC199 with Earle's salts (tenfold concentrate) (ICN); 4 ml heat inactivated swine serum (ICN); 10 ml sodium bicarbonate (7.5% in sterile water); 0.4 ml antibiotics solution (60 mg/ml benzylpenicillin+100 mg/ml streptomycin) and 0.72 ml heparin (5000 U/ml). This mixture was transferred to sterile flask and made up to 400 ml with sterile water.

Medium B (for cell culture)

To a sterile 250 ml measuring cylinder was added: 65 ml TC 199 (tenfold concentrate) with Earle's salts (ICN); 6.5 ml heat inactivated swine serum; 16.25 ml sodium bicarbonate (7.5% in sterile water); 0.65 ml antibiotics solution as above and 65 mg glutamine. This mixture was transferred to a sterile beaker and made up to 650 ml with sterile water.

Medium C=medium B+stimulant (zymosan)

The zymosan stimulant was prepared as follows: zymosan (200 mg) (supplied by Sigma) was added to PBS (20 ml). The mixture was boiled for 30 minutes and the volume restored to 20 ml with water. The zymosan was harvested by centrifugation at 500×g for 5 minutes, washed twice by resuspension in PBS (10 ml) and centrifugation. After the final separation, the zymosan was resuspended in 20 ml PBS and stored as 1 ml aliquots at −20° C.

650 ml medium B containing 15 ml zymosan=12.5 particles per cell was made up and then stored in 3 ml aliquots in freezer.

Test B was carried out in the following way:

Carrageenan-induced rat paw oedema test

Female rats, weight range 125–150 g were fasted overnight. One of the hind legs of each animal was marked with a line at the connection between the cuboid/navicular and calcaneus/talus bones. Groups of six rats were orally dosed at 10 ml/kg, in random order, with a given dose of the test compound given as a solution or suspension in 10% (w/v) aqueous acacia solution.

One hour after dosing, 0.1 ml of 1% (w/v) sterile carrageenan λ in normal saline was injected deeply into the plantar surface of the marked hind foot of each rat. The volume of the foot (up to the marked line) was measured immediately after injection using duplicate water displacement readings. Three hours after injection the foot volume was measured again and the percentage increase in foot volume relative to the initial reading was calculated.

The increase in foot volume (i.e. the degree of oedema) in drug treated animals when compared with that in the drug untreated control gave the degree of inhibition of paw oedema by the drug.

Compounds were considered to be active in this test if they produced a statistically significant (typically 20% or greater) inhibition of paw oedema in at least two out of three tests after oral dosing at 100 mg/kg. Statistical significance was assessed using the Student's t test for single dose studies and Dunnett's test for multiple dose studies. More advantageous compounds were active in both Tests A and B.

TABLE 1

| Example | Test A $IC_{50}$ µM | Test B % inhibition at 100 mg/kg |
|---|---|---|
| 1 & 2 | 38 | 27 |
| 3 | 6 | |
| 4 | 27 | 15 |
| 5 | 35* | 2 |
| 6 | | |
| 7 | 11 | 23 |
| 8 | 9 | 34 |
| 9 | 9 | 63 |
| 10 | 12 | 47 |
| 11 | 23 | 54 |
| 12 | 7 | 52 |
| 13 | 15 | 46 |
| 14 | 36 | 23 |
| 15 | 14 | 31 |
| 16 | 13 | 56 |
| 17 | 15 | 39 |
| 18 & 24 | 8* | 54 |
| 19 | 10 | 62 |
| 20 | 16 | 19 |
| 21 | 11 | |
| 22 | 28 | 38 |
| 23 | 25 | 11 |
| 25 | 12 | |
| 26 | 96 | |
| 27 | 27 | 9 |
| 28 | 22* | 46 |
| 29 | 22 | 13 |
| 30 | 14 | 10 |
| 31 | 3 | 15 |
| 32 | 2 | 7 |
| 33 | 40 | 33 |

TABLE 1-continued

| Example | Test A IC$_{50}$ μM | Test B % inhibition at 100 mg/kg |
|---|---|---|
| 34 | 28 | 36 |
| 35 | 13 | 32 |
| 36 | 28 | 21 |
| 37 | 17 | 31 |
| 38 | 30 | |
| 39 | 1* | 21 |
| 43 | 14* | |
| 44 | 15 | 26 |
| 45 | 16 | 15 |
| 46 | 15 | 40 |

*IC$_{50}$ μM based on 3 concentrations only namely 100, 10 and 1 μM.

TEST C

The most advantageous compounds of formula I were active in Tests A and B and also in the following test. Carrageenan-induced pleurisy in rats was carried out as described by Ackerman et al. J. Pharmacol. Exp. Therap. 1980, 215, 588–595. Migrating leukocytes were harvested by lavage of the thoracic cavity 72 h after injection of 0.3 ml 1% λcarrageenan in sterile isotonic saline. Test compounds were administered p.o. at the time of challenge and 24 h and 48 h thereafter.

For example the final products of Examples 7, 9, 11, 13, 16, 18 and 22 were active at 30 mg/kg in Test C and the final products of Examples 8, 10, 12 and 20 were active at 10 mg/kg or less in Test C.

Compounds which exhibit activity in both Tests A and C possess an advantageous profile of pharmacological activity unknown in commercially available antiinflammatory drugs and it is highly likely that such compounds possess significant advantages in terms of increased efficacy and/or reduced side-effects compared with known commercially available antiinflammatory drugs.

TEST D

Compounds of formula I suitable for the treatment of asthma were active in the three tests above and also in the late phase of the following test. Early and late phase bronchoconstriction in guinea-pigs following antigen challenge was determined by a variation of the method described by Hutson et al. Am. Rev. Respir. Dis. 1988, 137, 548–557. Guinea-pigs were sensitised by a single i.p. injection of 10 μg ovalbumin and challenged 15 to 17 days later by exposure to aerosolized antigen (4%) for five minutes, following pretreatment with mepyramine to prevent anaphylaxis. Changes in lung function were determined by whole body plethysmography at various times after challenge. Test compounds were administered p.o. 24 h and 2 h prior to challenge.

TEST E

The therapeutic activity of compounds of the present invention has also been demonstrated by an in vitro mixed lymphocyte reaction which is an in vitro correlate of in vivo cellular immune reactivity. A mixed lymphocyte reaction (MLR) occurs when lymphocytes from two genetically dissimilar individuals, or inbred strains of mice are cultured together. An MLR results in the activation and proliferation of lymphocytes, which is measured by the incorporation of radiolabelled thymidine into the cellular DNA synthesised during cell division. A 'one-way' MLR is used to determine the immunosuppressive activity of test compounds in vitro. In this reaction one population of spleen cells serves as the stimulator cells and is treated with mitomycin C to prevent cell division. Spleen cells from a second allogeneic population (responder cells) are untreated and when mixed with the stimulator cells are able to undergo division which is measured. The degree of proliferation is measured in the presence and absence of test compound to assess the immunosuppressive activity of the compound.

The techniques for carrying out lymphocyte proliferation assays including MLRs are well known, eg Bradley, pages 156–166, in Mishell and Shiigi, Eds. Selected Methods in Cellular Immunology (Freeman, San Francisco, 1980); and Battisto et al. methods in Enzymology 1987; 150: 83–91. Various slight modifications of these techniques are in use and that used herein is described in Gibb, Webber and Bowen, J Immunological Methods 1985; 81: 107–113. The immunomodulant activity of compounds was determined in a mixed lymphocyte reaction in the following manner:

Mixed Lymphocyte Reaction

Cell suspensions obtained from the spleens of female BALB/c and C57BL/6 strain mice of between 6 and 9 weeks of age were used as sources of responder and stimulator cells respectively. The mice were killed using a rising concentration of $CO_2$ and the spleens removed aseptically and teased using a scalpel and forceps to produce a single cell suspension in Hanks balanced salt solution (HBSS). The suspensions were filtered through cell strainers (Falcon), sedimented by centrifugation and resuspended in Tris-buffered ammonium chloride pH 7.2 (medium D) to lyse the erythrocytes. The cells were sedimented again and washed twice in HBSS before resuspending in complete RPMI 1640 tissue culture medium (medium E). The C57BL/6 cells were resuspended to 9 mls per spleen and a solution of mitomycin C at 400 μg/ml in medium E added to give a final concentration of 40 μg/ml. After incubation of the C57BL/6 cells at 37° C. for 30 minutes in an atmosphere of 5% $CO_2$ and 95% air, the cells were sedimented and washed 3 times in medium E. Both cell suspensions were diluted in medium E to 5×10$^6$ cells/ml 100 μl of each of the responder and stimulator cell suspensions were aliquoted into the wells of 96 well flat bottom microtitre plates containing 50 μl of test compound at an appropriate dilution (initially 50 μM diluted in medium E from a stock solution at 100 mM in dimethyl sulphoxide) giving a final test compound concentration of 10 μM (final dilution). Compounds active at this concentration were tested at further final dilution of 1 μM, 0.1 μM and 0.01 μM to determine the concentration of test compound which causes 50% inhibition of the immmune response (IC50). After four days of culture at 37° C. in a humidified atmosphere of 5% $CO_2$ and 95% air, 1 μCi of tritiated thymidine in 20 μl of medium E was added to each well and the plates incubated for a further 24 hours. Cells were then harvested onto Inotech G7 glass fibre filter mats using an Inotech cell harvester. The filters were transferred to vials to which 2 mls of Packard Emulsifier-Safe scintillation fluid was added and the radioactivity from the incorporated thymidine was counted in a Packard liquid scintillation counter. The counts per minute (CPM) reflect the degree of lymphocyte proliferation. The data were analysed to determine the percentage inhibition of lymphocyte proliferation by the test compound Compounds were deemed active if they reproducibly inhibited proliferation by ≧50% in the absence of toxicity at a concentration of ≦10 μM.

Medium D (for erythrocyte lysis)

Stock solutions 0.17M Tris. Tris base (20.6 g) was dissolved in distilled water (900 ml) and the pH adjusted to 7.65 with dilute hydrochloric acid. The volume was made up to 1000 ml with distilled water.

0.16M Ammonium chloride: Ammonium chloride (8.3 g) was dissolved in distilled water (1000 ml).

Working solutions

The Tris stock solution (10 ml) and ammonium chloride stock solution (90 ml) were mixed, the pH adjusted to 7.2 with dilute hydrochloric acid and the solution filter sterilised.

Medium E (for cell culture)

RPMI 1640 tissue culture medium containing 2.0 g/l sodium bicarbonate (ICN FLOW) supplemented with 5–10% serum supplement (foetal calf serum, Sigma or Nu-Serum, Collaborative Biomedical Products) 2 mM L-glutamine (ICN FLOW), 50 IU/ml penicillin (ICN FLOW), 50 µg/ml streptomycin (ICN FLOW) and $5 \times 10^{-5}$M 2-mercaptoethanol (SIGMA).

MLR data were expressed as the percentage inhibition of lymphocyte proliferation caused by the test compound, calculated by the formula $$\% \text{ inhibition} = 100 - \frac{\text{test} \times 100}{\text{control}}$$

where:

control=CPM thymidine incorporation by responder cells mixed with stimulator cells in the absence of compound test=CPM thymidine incorporation by responder cells mixed with stimulator cells in the presence of test compound.

The final products of the Examples listed below affected the MLR at a concentration of 10 µM in at least two out of three tests. The concentration of test compound which causes 50% inhibition of the immune response ($IC_{50}$ µM) for each compound is given below. A precise $IC_{50}$ value was not determined for those examples listed as having an $IC_{50}$ of >10.

| Example | 3 | 4 | 7 | 8 | 9 | 10 | 11 | 12 |
|---|---|---|---|---|---|---|---|---|
| $IC_{50}$ | 2.1 | >10 | 2.7 | 1.1 | 3.2 | 9.5 | 2.5 | 1.3 |
| Example | 13 | 15 | 16 | 17 | 19 | 20 | 21 | 23 |
| $IC_{50}$ | 3.2 | >10 | 63 | 2.8 | <1 | >10 | >10 | >10 |
| Example | 26 | 27 | 29 | 30 | 31 | 32 | 33 | 34 |
| $IC_{50}$ | >10 | >10 | >10 | >10 | 1.7 | 1.5 | >10 | 38.7 |
| Example | | 35 | 36 | 43 | 45 | 46 | | |
| $IC_{50}$ | | 53.8 | 45.3 | 2.01 | >10 | >10 | | |

The invention is illustrated by the following non-limitative Examples in which compositions of mixed solvents are given by volume. Novel compounds were characterised by one or more of the following: elemental analysis, nuclear magnetic resonance, infra-red and mass spectroscopy. Temperatures are given in degrees Celsius. The abbreviations HPLC (high performance liquid chromatography), THF (tetrahydrofuran), DMF (dimethylformamide), DMSO (dimethyl sulphoxide), IPA (propan-2-ol), IMS (industrial methylated spirit) and Wt (Weight), have been used in the Examples.

EXAMPLE 1

N,N-Dimethylformamide dimethyl acetal (23.3 ml) was added to 4-aminomethylpiperidine (20.0 g) in toluene (20 ml) and the mixture was boiled under reflux for 3 hours removing the water formed using a Dean and Stark apparatus to give a solution of 4-(dimethylaminomethyliminomethyl)piperidine. The mixture was cooled to ambient temperature and 2-bromoethyl phenyl ether (22.1 g) then triethylamine (24.3 ml) were added. The mixture was boiled under reflux for 10 hours and then evaporated to dryness. The residue was dissolved in 2M hydrochloric acid (200 ml) and heated on a steam bath for 24 hours. The mixture was cooled to ambient temperature and washed with dichloromethane. The aqueous layer was basified with 6M sodium hydroxide solution and extracted with dichloromethane to give an oil which was distilled at 186°–242° C. at 0.8 mbar. The distillate was dissolved in methanol (50 ml) and treated with concentrated aqueous ammonia solution (20 ml, specific gravity 0.88) and then left at ambient temperature for 18 hours. The solution was concentrated by evaporation and water (200 ml) was added. The mixture was extracted with dichloromethane to give an oil. The oil was dissolved in ether and treated with ethereal hydrogen chloride. A solid was collected by filtration and recrystallised from propan-2-ol/IMS to give 4-aminomethyl-1-(2-phenoxyethyl)piperidine dihydrochloride, m.p. 212°–214° C.

EXAMPLE 2

A mixture of 4-aminomethylpiperidine (25.0 g), acetophenone (25.6 ml), toluene (1 l) and a catalytic amount of p-toluenesulphonic acid was boiled under reflux for 6 hours, removing the water formed using a Dean and Stark apparatus. The mixture was cooled to approximately 70° C. then molten 2-bromoethyl phenyl ether (44.1 g) and triethylamine (30.5 ml) were added. The mixture boiled under reflux for 5 hours, then cooled and evaporated. The residue was heated on a steam bath for 5 hours with 6M hydrochloric acid (400 ml), to give after work up, 4-aminomethyl-1-(2-phenoxyethyl)piperidine dihydrochloride, m.p. 212°–214° C.

EXAMPLE 3

A mixture of 4-(dimethylaminomethyliminomethyl)piperidine (7.2 g, prepared as in Example 1), 2-bromoethyl 4-chlorophenyl ether (10.0 g), toluene (100 ml) and triethylamine (5.9 ml) was heated on a steam bath for 6 hours. The mixture was evaporated to dryness and the residue was dissolved in a 1:1 mixture of methanol/concentrated aqueous ammonia solution (S.G. 0.880, 80 ml). The mixture was stirred at ambient temperature for 16 hours and then evaporated to dryness. Water (50 ml) was added to the residue and the mixture was extracted with dichloromethane to give an oil. The oil was dissolved in ether and acidified with ethereal hydrogen chloride to give 4-aminomethyl-1-[2-(4-chlorophenoxy)ethyl]piperidine dihydrochloride m.p. 250°–252° C.

EXAMPLE 4

In a similar manner to Example 3, a mixture of 4-(dimethylaminomethyliminomethyl)piperidine (7.2 g), 3-bromopropyl phenyl ether (9.13 g), triethylamine (5.9 ml) and toluene (100 ml) was heated on a steam bath for 6 hours to give 4-aminomethyl-1-(3-phenoxypropyl)piperidine dihydrochloride, m.p. 235° C.

EXAMPLE 5

In a similar manner to Example 3, a mixture of 4-(dimethylaminomethyliminomethyl)piperidine (7.2 g), 2-bromoethyl 4-methoxyphenyl ether (9.8 g), triethylamine (5.9 g) and toluene (100 ml) was heated on a steam bath for 6 hours to give 4-aminomethyl-1-[2-(4-methoxyphenoxy)ethyl]piperidine dihydrochloride, m.p. 245°–247° C.

EXAMPLE 6

In a similar manner to Example 3, a mixture of 4-(dimethylaminomethyliminomethyl)piperidine (6.42 g), 2-bromoethyl 4-fluorophenyl ether (8.3 g), triethylamine (5.3 ml) and toluene (20 ml) was heated on a steam bath for 16 hours to give 4-aminomethyl-1-[2-(4-fluorophenoxy) ethyl]piperidine as an oil.

EXAMPLE 7

A mixture of 4-aminomethylpiperidine (3.58 g) and 4'-chloroacetophenone (4.85 g) in toluene (100 ml) was boiled under reflux with a catalytic amount of p-toluenesulphonic acid for 5 hours, removing the water formed by means of a Dean and Stark apparatus, to give a solution. The solution was cooled and 2-bromoethyl 4-methylphenyl ether (6.68 g) was added, followed by triethylamine (4.4 ml). This mixture was boiled under reflux for 6 hours then evaporated to dryness. 6M Hydrochloric acid (50 ml) was added to the residue and the mixture heated on a steam bath for 16 hours. The mixture was evaporated to near dryness, water (50 ml) was added and the mixture was washed with ether. The aqueous layer was basified with 2M sodium hydroxide solution and extracted with dichloromethane to give 4-aminomethyl-1-[2-(4-methylphenoxy) ethyl]piperidine as an oil. The oil was cooled in ice and 98% formic acid (5.0 ml) and formaldehyde (5.0 ml, 38% aqueous solution) were added. The mixture was heated on a steam bath for 4 hours then evaporated to near dryness and the residue treated with 2M hydrochloric acid (50 ml). The solution obtained was washed with dichloromethane, basified with 2M sodium hydroxide solution and extracted with dichloromethane to give an oil which was distilled at 150° C. at 0.13 mbar. This distillate was dissolved in ether and the solution acidified with ethereal hydrogen chloride. The precipitate was collected by filtration, washed with ether and recrystallised from absolute ethanol to give 4-dimethylaminomethyl-1-[2-(4-methylphenoxy)ethyl] piperidine dihydrochloride, m.p. 278°–280° C.

EXAMPLE 8

In a similar manner to Example 7, a mixture of 4-aminomethylpiperidine (2.9 g), 4'-chloroacetophenone (3.94 g), toluene (100 ml) and a catalytic amount of p-toluenesulphonic acid was boiled under reflux for five hours with removal of the water formed using a Dean and Stark apparatus. The mixture was cooled and treated with 2-bromoethyl 3-chlorophenyl ether (6.0 g) followed by triethylamine (3.54 ml). The mixture was boiled under reflux for 6 hours and then evaporated to dryness. 6M Hydrochloric acid (50 ml) was added and the mixture heated on a steam bath for 16 hours to give 4-aminomethyl-1-[2-(3-chlorophenoxy)ethyl]piperidine, as an oil. The oil, obtained on work up, was treated with 98% formic acid (5.0 ml) and formaldehyde (5.0 ml, 38% aqueous solution). The mixture was heated on a steam bath for 4 hours. After extractive work up as described in Example 7, the oil obtained was distilled at 120° C. at 0.13 mbar. The distillate was treated with ethereal hydrogen chloride to give 1-[2-(3-chlorophenoxy)ethyl]-4-(dimethylaminomethyl)piperidine dihydrochloride, m.p. 258°–260° C., after recrystallisation from absolute ethanol.

EXAMPLE 9

A mixture of 4-aminomethylpiperidine (7.0 g), benzaldehyde (5.77 g), toluene (70 ml) and a catalytic amount of p-toluenesulphonic acid was boiled under reflux for 7 hours with water removal using a Dean and Stark apparatus. The mixture was cooled to ambient temperature. 2-Bromoethyl phenyl ether (12.34 g) and triethylamine (8.5 ml) were added and the mixture was boiled under reflux for 5 hours. The mixture was evaporated to dryness and the residue dissolved in absolute ethanol (100 ml). Sodium borohydride (4.6 g) was added and the mixture was boiled under reflux for 18 hours. The mixture was evaporated to dryness and the residue partitioned between 2M hydrochloric acid and ethyl acetate. The aqueous layer was separated and basified with concentrated sodium hydroxide solution. This mixture was extracted with dichloromethane to give an oil which was dissolved in ether and treated with ethereal hydrogen chloride solution. A solid was collected by filtration and recrystallised from IMS to give 4-(N-benzylaminomethyl)-1-(2-phenoxyethyl)piperidine dihydrochloride, m.p. 246°–247° C.

EXAMPLE 10

4-Aminomethyl-1-(2-phenoxyethyl)piperidine (33.33 g) was cooled in ice and treated with 98% formic acid (33 ml) followed by formaldehyde (33 ml, 38% aqueous solution). The mixture was heated on a steam bath for 4 hours then evaporated to dryness. The residue was acidified with 3M hydrochloric acid and then washed with ether. The acid layer was basified with 2M sodium hydroxide solution and then extracted with dichloromethane to give an oil which was distilled at 150° C. at 0.13 mbar. The distillate was dissolved in ether and acidified with ethereal hydrogen chloride to give a solid which was collected by filtration, washed with ether, and recrystallised from absolute ethanol to give 4-(dimethylaminomethyl)-1-(2-phenoxyethyl)piperidine dihydrochloride, m.p. 268°–269° C.

EXAMPLE 11

In a similar manner to Example 10, a mixture of formaldehyde (4.14 ml, 37% aqueous solution), 4-(N-benzylaminomethyl)-1-(2-phenoxyethyl)piperidine (7.8 g) and 98% formic acid (4.42 ml) was heated on a steam bath for 2.5 hours to give 4-(N-benzyl-N-methylaminomethyl)-1-(2-phenoxyethyl)piperidine dihydrochloride, m.p. 260°–262° C.

EXAMPLE 12

In a similar manner to Example 10, a mixture of 4-aminomethyl-1-[2-(4-chlorophenoxy)ethyl]-piperidine (4.32 g), 98% formic acid (3.1 ml) and formaldehyde solution (2.9 ml, 35% aqueous solution) was heated on a steam bath for 3 hours to give 1-[2-(4-chlorophenoxy)ethyl]-4-dimethylaminomethylpiperidine dihydrochloride m.p. 259° C.

EXAMPLE 13

In a similar manner to Example 10, a mixture of 4-aminomethyl-1-[2-(4-fluorophenoxy)ethyl]piperidine (2.69 g, see Example 6), 98% formic acid (2.5 ml) and formaldehyde (2.5 ml, 35% aqueous solution) was heated on a steam bath for 4 hours to give 4-dimethylaminomethyl-1-[2-(4-fluorophenoxy)ethyl]piperidine dihydrochloride, m.p. 260°–262° C.

EXAMPLE 14

In a similar manner to Example 10, a mixture of 4-aminomethyl-1-[2-(4-methoxyphenoxy)ethyl]piperidine (4.35 g), 98% formic acid (3.2 ml) and formaldehyde (3.0 ml, 35% aqueous solution) was heated on a steam bath for 3 hours to give 4-dimethylaminomethyl-1-[2-(4-methoxyphenoxy)ethyl]piperidine dihydrochloride, m.p. 250° C.

EXAMPLE 15

In a similar manner to Example 10, a mixture of 4-aminomethyl-1-(3-phenoxypropyl)piperidine (3.25 g), 98% formic acid (2.5 ml) and formaldehyde (2.4 ml, 35% aqueous solution) was heated on a steam bath for 3 hours to give 4-dimethylaminomethyl-1-(3-phenoxypropyl) piperidine dihydrochloride, m.p. 244° C.

EXAMPLE 16

A mixture of 4-(2-dimethylaminoethyl)piperidine dihydrochloride (7.0 g), 2-bromoethyl 4-methylphenyl ether (6.6 g), triethylamine (12.75 ml) and DMF (50 ml) was heated on a steam bath for 16 hours. The mixture was poured into ice/water (500 ml), basified with 2M sodium hydroxide solution and extracted with dichloromethane. The combined organic extracts were washed with water and then extracted with 2M hydrochloric acid. The combined acidic layers were basified with 2M sodium hydroxide solution and then extracted with dichloromethane to give an oil. The oil was distilled at 120° C. at 0.05 mbar and the distillate was dissolved in ether, acidified with ethereal hydrogen chloride solution and filtered. The solid obtained was washed with ether and recrystallised from absolute ethanol to give 4-(2-dimethylaminoethyl)-1-[2-(4-methylphenoxy)ethyl] piperidine dihydrochloride m.p. 281°–283° C.

EXAMPLE 17

In a similar manner to Example 16, a mixture of 4-(2-dimethylaminoethyl)piperidine dihydrochloride (5.5 g), 2-bromoethyl 4-fluorophenyl ether (5.26 g), triethylamine (13.4 ml) and DMF (50 ml) was heated on a steam bath for 16 hours to give 4-(2-dimethylaminoethyl)-1-[2-(4-fluorophenoxy)ethyl]piperidine dihydrochloride, m.p. 260°–262° C.

EXAMPLE 18

2-Bromoethyl phenyl ether (4.94 g) was added to a mixture of 4-[2-(N-benzyl-N-methylamino)ethyl]piperidine dihydrochloride (7.5 g), DMF (50 ml) and triethylamine (13.7 ml) The mixture was heated on a steam bath for 18 hours and then poured into water (300 ml) and acidified with 2M hydrochloric acid. The mixture was washed with ether then basified with 2M sodium hydroxide solution and extracted with dichloromethane to give a gum. The gum was dissolved in petroleum ether b.p. 60°–80° C., treated with charcoal and hot filtered. The filtrate was evaporated and the residual oil was dissolved in ether, acidified with ethereal hydrogen chloride, and filtered. The solid obtained was washed with ether and recrystallised from absolute ethanol to give 4-[2-(N-benzyl-N-methylamino)ethyl]-1-(2-phenoxyethyl)piperidine dihydrochloride, m.p. 276°–278° C.

EXAMPLE 19

A mixture of 4-(2-dimethylaminoethyl)piperidine dihydrochloride (7.0 g), 2-bromoethyl 3-chlorophenyl ether (7.2 g), triethylamine (12.75 ml) and DMF (50 ml) was heated on a steam bath for 16 hours then worked up as described in Example 16 to give 1-[2-(3-chlorophenoxy)ethyl]-4-(2-dimethylaminoethyl)piperidine dihydrochloride, m.p. 260°–264° C.

EXAMPLE 20

A mixture of 4-(2-piperidinoethyl)piperidine (3.27 g), 2-bromoethyl phenyl ether (3.35 g), triethylamine (2.3 ml) and DMF (50 ml) was heated on a steam bath for 16 hours. The mixture was worked up as described in Example 16. The crude solid hydrochloride was treated with sodium bicarbonate solution and the mixture extracted with dichloromethane to give the free base which was purified by flash chromatography on silica using methanol/triethylamine, 99:1 as the mobile phase. The oil obtained was dissolved in ether and acidified with ethereal hydrogen chloride to give 1-(2-phenoxyethyl)-4-(2-piperidinoethyl)piperidine dihydrochloride, m.p. 285° C.

EXAMPLE 21

A mixture of 2-bromoethyl 2-methoxyphenyl ether (7.5 g), 4-(2-dimethylaminoethyl)piperidine dihydrochloride (7.44 g), triethylamine (18.1 ml) and DMF (50 ml) was heated on a steam bath for 18 hours. The mixture was poured into ice/water (500 ml) and basified with 2M sodium hydroxide. The product was extracted into dichloromethane to give an oil. The oil was triturated with ether. The ether was decanted off and evaporated to give crude 4-(2-dimethylaminoethyl)-1-[2-(2-methoxyphenoxy)ethyl] piperidine (4.58 g) which was added to glacial acetic acid (17 ml) and 48% hydrobromic acid (57 ml). The mixture was heated on a steam bath for 4 hours and then evaporated to dryness. The residue was dissolved in water, basified with 2M sodium hydroxide solution and extracted with dichloromethane to give an oil. The oil was dissolved in ether and acidified with ethereal hydrogen chloride The precipitate was collected by filtration and recrystallised from propan-2-ol to give 2-{2-[4-(2-dimethylaminoethyl)piperidino] ethoxy}phenol dihydrochloride m.p. 273°–275° C.

EXAMPLE 22

A mixture of 4-(2-dimethylaminoethylidene)-1-(2-phenoxyethyl)piperidine (2.0 g) (The product of Example 37 was treated with aqueous sodium bicarbonate solution and ether. The ether was separated, washed, dried and evaporated to give the free base.) in IMS (200 ml) and a catalytic amount of 10% palladium on charcoal was hydrogenated at atmospheric pressure for 5 hours. The catalyst was removed by filtration. The filtrate was evaporated to give an oil which was dissolved in ether and then acidified with ethereal hydrogen chloride. The precipitate was collected by filtration and recrystallised from IMS to give 4-(2-dimethylamino-ethyl)-1-(2-phenoxyethyl)piperidine dihydrochloride, m.p. 286°–288° C.

EXAMPLE 23

In a similar manner to Example 22, 1-(2-phenoxyethyl)-4-[2-(pyrrolidin-1-yl)ethylidene]piperidine (from Example 38) was hydrogenated to give 1-(2-phenoxyethyl)-4-[2-pyrrolidin-1-yl)ethyl]piperidine dihydrochloride, m.p. 270° C.

EXAMPLE 24

In a similar manner to Example 22, 4-[2-(N-benzyl-N-methylamino)ethylidene]-1-(2-phenoxyethyl)piperidine (from Example 39) was hydrogenated to give 4-[2-(N-benzyl-N-methylamino)ethyl]-1-(2-phenoxyethyl) piperidine dihydrochloride, m.p. 274°–275° C.

EXAMPLE 25

In a similar manner to Example 22, 1-[2-(4-chlorophenoxy)ethyl]-4-(2-dimethylaminoethylidene)

piperidine (Example 40) was hydrogenated to give 1-[2-(4-chloro-phenoxy)ethyl]-4-(2-dimethylaminoethyl)piperidine dihydrochloride, m.p. 266°–267° C.

EXAMPLE 26

In a similar manner to Example 22, 4-(2-dimethylaminoethylidene)-1-[2-(2-methoxyphenoxy)thyl] piperidine (Example 41) was hydrogenated to give 4-(2-dimethylaminoethyl)-1-[2-(2-methoxyphenoxy)ethyl] piperidine dihydrochloride, m.p. 246°–247° C.

EXAMPLE 27

In a similar manner to Example 22, 4-(2-dimethylaminoethylidene) 1-[2-(4-methoxyphenoxy)ethyl] piperidine (Example 42) was hydrogenated to give 4-(2-dimethylamino-ethyl)-1-[2-(4-methoxyphenoxy)ethyl] piperidine dihydrochloride, m.p. 254°–256° C.

EXAMPLE 28 n-Butyllithium (9.66 ml, 2.5M solution in hexanes) was added dropwise to a suspension of (3-dimethylaminopropyl) triphenylphosphonium bromide (11.37 g) in dry THF (70 ml) at 0° C. under nitrogen with stirring. The mixture was stirred at 0° C. for 30 minutes and then 1-(2-phenoxyethyl)-4-piperidone (5.25 g) in THF (20 ml) was added dropwise over 5 minutes. The mixture was stirred at 0° C. for one hour, warmed to ambient temperature and then boiled under reflux for 18 hours under nitrogen. The mixture was evaporated to dryness. Dichloromethane (100 ml) was added to the residue and the mixture acidified with 2M hydrochloric acid (50 ml). The mixture was separated and the organic layer extracted with dilute hydrochloric acid. The combined acidic layers were washed with dichloromethane, basified with 2M sodium hydroxide solution and extracted with ether to give an oil. The oil was extracted with hot petroleum ether b.p. 60°–80° C. The petroleum ether was decanted off and evaporated to yield an oil (2.45 g) which was dissolved in IMS (100 ml) and hydrogenated at 1 atmosphere over 10% palladium charcoal (catalytic amount). The catalyst was removed by filtration and the filtrate evaporated to give an oil which was purified by flash chromatography on silica, using methanol and then methanol/triethylamine (99:1) as the mobile phase, to give the product as an oil. The oil was dissolved in ether, acidified with ethereal hydrogen chloride and filtered to give 4-(3-dimethylaminopropyl)-1-(2-phenoxyethyl)piperidine dihydrochloride, m.p. 226°–227° C.

EXAMPLE 29

In a similar manner to Example 28, n-butyllithium (25.2 ml, 2.5M solution in hexanes) was added to a suspension of (2-dimethylaminoethyl)triphenylphosphonium bromide (28.7 g) in dry THF (200 ml). This mixture was then treated with a solution of 1-(3-phenoxypropyl)-4-piperidone (14.7 g) in THF (20 ml). The oil obtained after work up (6.24 g) was hydrogenated in IMS at 1 atmosphere over 10% palladium charcoal over 16 hours. The catalyst was removed by filtration. The filtrate was evaporated and the residue was dissolved in petroleum ether, b.p. 60°–80° C. The solution was dried and evaporated to give an oil which was dissolved in ether and acidified with ethereal hydrogen chloride to yield a precipitate. The precipitate was collected by filtration and recrystallised from IMS to give 4-(2-dimethylaminoethyl)-1-(3-phenoxypropyl)piperidine dihydrochloride, m.p. 294°–295° C.

EXAMPLE 30

In a similar manner to Example 28, a mixture of n-butyllithium (20 ml, 2.5M solution in hexanes) was added to a suspension of (2-dimethylaminoethyl) triphenylphosphonium bromide (22.8 g) in THF (200 ml) The mixture was treated with 1-(4-phenoxybutyl)-4-piperidone (12.35 g)in dry THF (20 ml). The oil obtained on work up was hydrogenated in IMS at 1 atmosphere over 10% palladium charcoal over 16 hours to give 4-(2-dimethylaminoethyl)-1-(4-phenoxybutyl)piperidine dihydrochloride, m.p. 268°–270° C.

EXAMPLE 31

A mixture of 4-aminomethylpiperidine (5.0 g), 4'-chloroacetophenone (6.77 g), p-toluenesulphonic acid (catalytic amount) and toluene (50 ml) was boiled under reflux for 8 hours while removing the water formed using a Dean and Stark apparatus. The mixture was cooled to ambient temperature and 2-bromoethyl phenyl ether (8.84 g) and triethylamine (6.1 ml) were added. The mixture was boiled under reflux for 2 hours and evaporated to dryness. The residue was dissolved in ethanol (100 ml) and sodium borohydride (3.4 g) was added. The mixture was boiled under reflux for 18 hours and then evaporated to dryness. The residue was dissolved in 2M hydrochloric acid, washed with ethyl acetate, basified with 5M sodium hydroxide solution and the mixture extracted with dichloromethane to give an oil. The oil was dissolved in ether and treated with ethereal hydrogen chloride solution to give a solid which was collected by filtration and recrystallised from absolute ethanol to give 4-[1-(4-chlorophenyl)ethylaminomethyl-]-1-(2-phenoxyethyl)piperidine dihydrochloride, m.p. 220° C.

EXAMPLE 32

In a similar manner to Example 31, a mixture of 4-(2-aminoethyl)piperidine (5.0 g), 4'-chloroacetophenone (6.04 g), p-toluenesulphonic acid (catalytic amount) and toluene (100 ml) was boiled under reflux for 10 hours with water removal using a Dean and Stark apparatus. The mixture was cooled to ambient temperature and 2-bromoethyl phenyl ether (7.85 g) and triethylamine (5.4 ml) added. The mixture was boiled under reflux for 6 hours. The solvent was evaporated off and the residue dissolved in ethanol (100 ml) and sodium borohydride (3.4 g) was added. The mixture was boiled under reflux for 4 hours then worked up to give an oil which was purified by flash column chromatography on silica using ethyl acetate/triethylamine (95:5) as the mobile phase to give 4-{2-[1-(4-chlorophenyl)ethylamino]ethyl}-1-(2-phenoxyethyl)piperidine as an oil.

EXAMPLE 33 a) Acetic anhydride (8.72 g) was added with stirring to a mixture of 4-aminomethyl-1-(2-phenoxyethyl) piperidine (20.0 g) in pyridine (85 ml) containing 4-dimethylaminopyridine (catalytic amount) with cooling to maintain ambient temperature. The mixture was stirred overnight at ambient temperature and then evaporated to dryness. Water was removed by adding toluene and removing the toluene by distillation. The residue was dissolved in water (100 ml) and 2M hydrochloric acid (50 ml). The solution was washed with dichloromethane, basified with concentrated sodium hydroxide solution and extracted with dichloromethane to give N-[1-(2-phenoxyethyl)piperid-4-ylmethyl]acetamide as an oil which solidified on standing, m.p. 79°–80° C.

b) A solution of the acetamide from part a) (6.05 g) in dry THF (50 ml) was added dropwise with stirring to a suspension of sodium hydride (0.88 g, 60% dispersion in mineral oil) in dry THF (40 ml) with cooling at ambient temperature under nitrogen. The suspension was stirred for 30 minutes and then a solution of ethyl iodide (3.42 g) in dry THF (20 ml) was added dropwise with stirring. The mixture was stirred at ambient temperature for 5 hours and then heated on a steam bath with stirring for 18 hours. The mixture was evaporated to dryness. The residue was dissolved in 2M hydrochloric acid and washed with ethyl acetate. The aqueous layer was basified with concentrated sodium hydroxide solution and then extracted with dichloromethane to give an oil. The oil was extracted with boiling petroleum ether b.p. 60°–80° C. and then the extracts were combined and evaporated to dryness. The residue was stirred with petroleum ether, b.p. 60°–80° C. (100 ml). The solution was decanted from the residue, dried and evaporated to give N-ethyl-N-[1-(2-phenoxyethyl)piperid-4-ylmethyl]acetamide.

c) Lithium aluminium hydride solution (11.5 ml, 1M solution in THF) was added to dry THF (11 ml) with stirring at 0° C. under nitrogen. The solution was stirred for 5 minutes and then concentrated sulphuric acid (0.31 ml) was added dropwise at 0° C. The mixture was stirred for 15 minutes then a solution of the product from b) (2.65 g) in dry THF (15 ml) was added dropwise at 0° C. The mixture was allowed to warm up to ambient temperature with stirring and then stirred at ambient temperature for 3 hours. The mixture was cooled in ice and a mixture of water and THF (1:1) (2 ml) was added dropwise, followed by 2M sodium hydroxide solution (7 ml). The mixture was filtered and evaporated to dryness. The residue was basified with 2M sodium hydroxide solution and extracted with dichloromethane to give an oil. The oil was dissolved in ether and treated with ethereal hydrogen chloride solution to give a solid which was collected by filtration and recrystallised from propan-2-ol to give 4-diethylaminomethyl-1-(2-phenoxyethyl)piperidine dihydrochloride, m.p. 195°–197° C.

EXAMPLE 34

In a similar manner to Example 33c), N-[1-(2-phenoxyethyl)piperid-4-ylmethyl]acetamide (13.0 g) was reduced to give 4-(ethylaminomethyl)-1-(2-phenoxyethyl) piperidine dihydrochloride, m.p. 268°–270° C.

EXAMPLE 35

A solution of 4-(ethylaminomethyl)-1-(2-phenoxyethyl) piperidine (3.0 g) in 98% formic acid (2.2 ml) and 37% aqueous formaldehyde (2.06 ml) was heated on a steam bath for 5 hours. Work up as described in Example 10 gave an oil which was dissolved in ether and treated with ethereal hydrogen chloride solution to give a solid which was collected by filtration and recrystallised from absolute ethanol to give 4-(N-ethyl-N-methylaminomethyl)-1-(2-phenoxyethyl)piperidine dihydrochloride, m.p. 248°–250° C.

EXAMPLE 36 a) A solution of propionyl chloride (2.37 g) in dichloromethane (10 ml) was added dropwise to a solution of 4-aminomethyl-1-(2-phenoxyethyl)piperidine (6.0 g) in dichloromethane (50 ml) and triethylamine (3.9 ml) at 0° C. The solution was allowed to warm up to ambient temperature with stirring and then stirred at this temperature for a further 2 hours. More propionyl chloride (0.3 ml) was added at ambient temperature and the solution stirred for a further half-hour. Further propionyl chloride (0.3 ml) was added and the mixture stirred for 1 hour. The mixture was extracted with 2M hydrochloric acid. The combined acidic extracts were washed with ethyl acetate, then basified with sodium hydroxide solution and extracted with dichloromethane to give an oil which solidified on standing to give N-[1-(2-phenoxyethyl)piperid-4-ylmethyl] propionamide, m.p. 85°–86° C.

b) The product from part a) was reduced in a similar manner to Example 33 c) to give 1-(2-phenoxyethyl)-4-(propylaminomethyl)piperidine dihydrochloride, m.p. 265°–267° C.

EXAMPLE 37 n-Butyllithium (9.13 ml, 2.5M solution in hexanes) was added to a suspension of (2-dimethylaminoethyl) triphenylphosphonium bromide (9.46 g) in dry THF (60 ml) under nitrogen at 0° C. over 5 minutes. The mixture was stirred at 0° C. for 30 minutes and then 1-(2-phenoxyethyl)-4-piperidone (5.0 g) in THF (15 ml) was added dropwise over 5 minutes. The mixture was warmed to ambient temperature and then heated at 60° C. for 5 hours. The mixture was left at ambient temperature for 18 hours and then quenched with water and diluted with ethyl acetate. 2M Hydrochloric acid was added and the mixture was separated. The organic layer was extracted with 2M hydrochloric acid and the combined acidic layers were basified and extracted with dichloromethane to give an oil. The oil was purified by flash column chromatography on silica using dichloromethane and then dichloromethane/methanol (1:1) as the mobile phase. The oil obtained after chromatography was dissolved in ether and treated with ethereal hydrogen chloride. The ether was decanted off and the residual semi-solid was triturated with acetone/ether (1:1) and filtered to give a solid which was recrystallised from IMS to give 4-(2-dimethylaminoethylidene)-1-(2-phenoxyethyl)piperidine dihydrochloride, m.p. 234°–235° C.

EXAMPLES 38–42

Examples 38–42 were carried out in a similar manner to Example 37 as summarised in Table 1 below. A compound of formula IX, in which ALK$^1$ represents —(CH$_2$)$_2$—, Y represents a piperidine ring which has ALK$^1$ attached at the 1-position and the oxygen attached at the 4-position and R$_1$, R$_2$ and R$_3$ are as given in Table 1, was reacted with a compound of formula Xa in which R$_4$ represents hydrogen, ALK$^2$ represents methylene, X represents bromide and R$_5$ and R$_6$ are as given in Table 1.

TABLE 1

| Example | IX $R_1R_2R_3$ | Wt of IX (g) | THF (ml) | Xa $R_5$ | Xa $R_6$ | Wt of Xa (g) | n-BuLi* ml | Notes |
|---|---|---|---|---|---|---|---|---|
| 38 | H | 3.6 | 55 | —(CH$_2$)$_4$— | | 7.2 | 6.5 | |
| 39 | H | 3.3 | 60 | CH$_3$ | PhCH$_2$ | 7.3 | 6.0 | |
| 40 | 4-Cl | 5.0 | 80 | CH$_3$ | CH$_3$ | 9.0 | 7.9 | (1) |
| 41 | 2-OCH$_3$ | 5.0 | 80 | CH$_3$ | CH$_3$ | 9.1 | 8.0 | (1) |
| 42 | 4-OCH$_3$ | 3.0 | 45 | CH$_3$ | CH$_3$ | 5.5 | 4.8 | (1) |

(1) The acidic extracts were basified with dilute sodium hydroxide solution and extracted into ether to give the product in free base form, as an oil.
*2.5M solution in hexanes.

The compounds prepared in Table 1 were as follows:

EXAMPLE 38

1-(2-Phenoxyethyl)-4-[2-(pyrrolidin-1-yl)ethylidene] piperidine dihydrochloride hemihydrate, m.p. 227°–228° C.

EXAMPLE 39

4-[2-(N-Benzyl-N-methylamino)ethylidene]-1-(2-phenoxyethyl]piperidine dihydrochloride, m.p. 225°–226° C.

EXAMPLE 40

1-[2-(4-Chlorophenoxy)ethyl]-4-(2-dimethylaminoethylidene)piperidine as an oil.

EXAMPLE 41

4-(2-Dimethylaminoethylidene)-1-[2-(2-methoxyphenoxy)ethyl]piperidine as an oil.

EXAMPLE 42

4-(2-Dimethylaminoethylidene)-1-[2-(4-methoxyphenoxy)ethyl]piperidine as an oil.

EXAMPLE 43 n-Butyllithium (4.1 ml, 2.5M solution in hexanes) was added to a mixture of 2-dimethylaminoethyl triphenylphosphonium bromide (4.71 g) in dry THF (50 ml) with stirring at 0° C. under nitrogen. The mixture was stirred at 0° C. for 30 minutes and then a solution of N-(2-phenoxyethyl)piperidine-3-carbaldehyde (2.41 g) in THF (5 ml) was added dropwise at 0° C. with stirring. The mixture was allowed to warm to ambient temperature and then boiled under reflux for 18 hours under nitrogen. The mixture was evaporated to dryness under reduced pressure and then treated with dilute hydrochloric acid. The mixture was washed with dichloromethane, basified with 2M sodium hydroxide solution and extracted with dichloromethane to give an oil. The oil was triturated with petroleum ether b.p. 40°–60° C., and the supernatant petroleum ether decanted off to leave an oil. The oil was stored at 5° C. for 64 hours, during which time a fine crystalline solid formed. Petroleum ether b.p. 40°–60° C. was added and the mixture was filtered to give a solid which was discarded. The filtrate was evaporated to yield a pale yellow oil, which was identified as (E)-3-(3-dimethylamino-1-propenyl)-1-(2-phenoxyethyl)piperidine. A portion of this oil (2.0 g) was dissolved in ether and acidified with ethereal citric acid to give a precipitate which was collected by filtration, washed with acetone and dried to give (E)-3-(3-dimethylamino-1-propenyl)-1-(2-phenoxyethyl)piperidine dicitrate, m.p. 65°–70° C.

EXAMPLE 44

(E)-3-(3-dimethylamino-1-propenyl)-1-(2-phenoxyethyl) piperidine (5.0 g) was hydrogenated in a similar manner to Example 22 to give 3-(3-dimethylaminopropyl)-1-(2-phenoxyethyl)piperidine dihydrochloride, m.p. 204°–206° C. (with decomposition).

EXAMPLE 45

A mixture of 3-chloromethyl-1-(2-phenoxyethyl) piperidine hydrochloride (4.2 g), pyrrolidine (1.23 g), sodium bicarbonate (3.7 g), potassium iodide (catalytic amount) and IMS (100 ml) was boiled under reflux for 48 hours. The mixture was evaporated to dryness under reduced pressure and ether was added to the residue. The mixture was filtered. The filtrate was evaporated under reduced pressure to give a residue to which pyrrolidine (30 ml) was added. This mixture was boiled under reflux for 16 hours. The excess pyrrolidine was removed under reduced pressure and the residue was purified by azeotropic distillation with toluene. The residue was partitioned between ether and water and the ether layer was separated. The aqueous layer was extracted with ether. The combined ether extracts yielded an oil which was dissolved in ether and acidified with ethereal citric acid to give a solid which was collected by filtration to give 1-(2-phenoxyethyl)-3-(pyrrolidin-1-ylmethyl)piperidine dicitrate, m.p. 69° C. (with decomposition).

EXAMPLE 46

A mixture of 3-chloromethyl-1-(2-phenoxyethyl) piperidine (2.8 g) and piperidine (15 ml) was heated on a steam bath for 24 hours. The excess piperidine was removed under reduced pressure and the residue purified by azeotropic distillation with toluene. The residue was dissolved in ether/water and then basified to pH 14. The mixture was extracted with ether and the combined ether extracts yielded an oil which was dissolved in ether and acidified with ethereal citric acid to give a solid which was collected by filtration to give 1-(2-phenoxyethyl)-3-(piperidin-1-ylmethyl)piperidine dicitrate, m.p. 88°–89° C. (with decomposition).

PREPARATION OF STARTING MATERIALS

Starting materials, not detailed below, were commercially available and may be found by reference to the Fine Chemicals Directory or suppliers' catalogues.

[2-(Pyrrolidin-1-yl)ethyl]triphenylphosphonium bromide a) A mixture of 2-bromoethyl phenyl ether (20.0 g), triphenylphosphine (26.2 g) and phenol (200 g) was heated at 90° C. with stirring for 48 hours. The mixture was cooled to approximately 40° C. and added to ether (1500 ml). The ether was decanted off and the residual oil was triturated with ether until a solid was obtained. The solid was collected by filtration to give (2-phenoxyethyl)triphenylphosphonium bromide.

b) A mixture of the product from a) (10 g), pyrrolidine (5.0 g) and DMSO (20 ml) was heated at 40° C. for 10 minutes with stirring. The mixture was poured into ether. The ether was decanted off and the residual oil was triturated with ether to give a solid which was collected by filtration to give (2-(pyrrolidin-1-yl)ethyl] triphenylphosphonium bromide, m.p. 188°–190° C.

The other phosphonium salts required as starting materials in Table 1 were prepared in a similar manner, by reacting (2-phenoxyethyl)triphenylphosphonium bromide with the appropriate amine.

4-[2-(Chlorophenoxy)ethyl]piperidone

A mixture of 2-bromoethyl 4-chlorophenyl ether (10.0 g), 4-piperidone (6.5 g), sodium bicarbonate (7.14 g) and IMS (100 ml) was boiled under reflux for 24 hours. The mixture was cooled and the solvent removed under reduced pressure. Water was added to the residue and the mixture was extracted with dichloromethane. The combined organic extracts were then extracted with dilute hydrochloric acid and the acidic extracts were filtered and then basified with sodium hydroxide solution. The mixture obtained was extracted with ether to give 4-[2-(chlorophenoxy)ethyl] piperidone as a solid.

The other 1-substituted 4-piperidones required as starting materials in Table 1 were prepared in a similar manner by reacting 4-piperidone with the appropriately substituted commercially available halo ether.

(3-Dimethylaminopropyl)triphenylphosphonium bromide a) 1,3-Dibromopropane (28.8 ml) was added to a solution of triphenylphosphine (15.0 g) in toluene (30 ml). The mixture was stirred at 70° C. under nitrogen for 16 hours, then cooled, diluted with ether (150 ml) and filtered to give 3-bromopropyltriphenylphosphonium bromide.

b) A solution of dimethylamine in IMS (80 ml of a 33% solution) was added to a suspension of the product from a) (12.5 g) in absolute ethanol (160 ml) at 0° C. The mixture was stirred at ambient temperature for 5 hours and then left to stand at this temperature for 18 hours. The solvent was removed under reduced pressure and the residue was triturated with dichloromethane. The mixture was filtered to give (3-dimethylaminopropyl) triphenylphosphonium bromide, m.p. 275° C.

2-Chloroethyl 4-chlorophenyl ether

A mixture of 4-chlorophenol (100 g), 1-bromo-2-chloroethane (335 g), potassium carbonate (129 g) and acetone (2 l) was boiled under reflux with stirring for 18 hours. The mixture was evaporated to dryness under reduced pressure and then dichloromethane was added to the cool residue. The mixture was filtered and the filtrate washed with 5M sodium hydroxide solution, water, dried, filtered and evaporated to give 2-chloroethyl 4-chlorophenyl ether as an oil.

4-(2-Dimethylaminoethyl)piperidine a) Benzoyl chloride (25.8 ml) in dichloromethane (20 ml) was added dropwise over 30 minutes to a mixture of 4-(2-hydroxyethyl)piperidine (26 g) in dichloromethane (250 ml) and triethylamine (16.3 ml) at 0° C. The mixture was allowed to warm to ambient temperature and stirred at this temperature for 1 hour. The mixture was washed with sodium bicarbonate solution and then dried and evaporated to give a colourless oil. The oil was dissolved in 1,4-dioxane (250 ml) and then a solution of sodium hydroxide (5.0 g) in water (20 ml) was added and the mixture stirred at ambient temperature for 16 hours and then at 60° C. for 6 hours. The mixture was evaporated to near dryness, basified with 2M sodium hydroxide solution and the product extracted into dichloromethane to give 1-benzoyl-4-(2-hydroxyethyl)piperidine as an oil.

b) Thionyl chloride (0.38 ml) was added dropwise to a solution of the product from a) (1.0 g) in chloroform (10 ml) with stirring. The mixture was stirred at ambient temperature for 1 hour and then boiled under reflux for 30 minutes. The mixture was evaporated to dryness and the residue was dissolved in dichloromethane, washed with sodium bicarbonate solution, dried and evaporated to give 1-benzoyl-4-(2-chloroethyl) piperidine as an oil.

c) A mixture of the product from b) (11.61 g) and a 33% solution of dimethylamine in absolute ethanol (100 ml) was boiled under reflux for 16 hours. The mixture was evaporated to dryness and 2M hydrochloric acid (50 ml) was added. The mixture was washed with ether and then the acidic layer was basified with 2M sodium hydroxide solution and the product extracted into dichloromethane to give a gum. The gum was dissolved in petroleum ether b.p. 60°–80° C. and treated with charcoal, then filtered and the filtrate evaporated to give an oil. A portion of the oil (1.5 g) was dissolved in ether and acidified with ethereal oxalic acid to give 1-benzoyl-4-(2-dimethylaminoethyl)piperidine oxalate, m.p. 82°–84° C.

d) The oil from c) (6.0 g) and 6M hydrochloric acid (50 ml) was heated on a steam bath for 16 hours. The mixture was evaporated to near dryness and basified with 2M sodium hydroxide solution. The mixture was extracted with dichloromethane to give an oil which was dissolved in ether and acidified with ethereal hydrogen chloride. The mixture was filtered to give a solid which was recrystallised from IMS/IPA (1:1) to give 4-(2-dimethylaminoethyl)piperidine dihydrochloride, m.p. 242°–245° C.

4-(2-Piperidinoethyl)piperidine a) A mixture of 1-benzoyl-4-(2-chloroethyl)piperidine (5.86 g), piperidine (11.52 ml) and IMS (100 ml) was boiled under reflux for 10 hours. The mixture was evaporated to near dryness and then dried by azeotropic distillation with toluene. The residue was dissolved in dichloromethane, washed with 2M sodium hydroxide solution and then brine. The separated organic layer was extracted with 2M hydrochloric acid and the combined acidic layers were basified with 2M sodium hydroxide solution and then extracted with dichloromethane to give 1-benzoyl-4-(2-piperidinoethyl) piperidine as an oil.

b) The product from a) (5.81 g) and 6M hydrochloric acid (100 ml) were heated on a steam bath for 16 hours. The mixture was evaporated to dryness then diluted with water (100 ml) and then washed with dichloromethane. The aqueous layer was basified with 2M sodium hydroxide solution and then extracted with dichloromethane to give 4-(2-piperidinoethyl)piperidine as an oil.

4-[2-(N-Benzyl-N-methylamino)ethyl]piperidine a) A mixture of 1-benzoyl-4-(2-chloroethyl)piperidine (11.61 g), N-methylbenzylamine (16.75 g) and IMS (100 ml) was boiled under reflux for 16 hours. The mixture was evaporated to dryness and then 4M hydrochloric acid (50 ml) was added to the residue. The mixture was washed with ether and the acidic layer was then basified with 4M sodium hydroxide solution and extracted with dichloromethane to give an oil. Excess amine was distilled off at 13 mbar and the residue was triturated with petroleum ether b.p. 40°–60° C. The supernatant petroleum ether was decanted off and the residual oil was dried under vacuum to give 1-benzoyl-4-[2-(N-benzyl-N-methylamino)ethyl]piperidine. A small portion of the oil was dissolved in ether and acidified with ethereal oxalic acid. The supernatant liquid was decanted off and the solid residue was triturated with acetone and filtered to give the oxalate salt, m.p. 141°–142° C.

b) The oil from a) (5.0 g) and 6M hydrochloric acid (50 ml) were heated together on a steam bath for 16 hours. The mixture was evaporated to near dryness and the residue basified with 2M sodium hydroxide solution. The mixture was extracted with dichloromethane to give an oil which was dissolved in ether, acidified with ethereal oxalic acid and then filtered to give a solid which was recrystallised from IMS to give 4-[2-(N-benzyl-N-methylamino)ethyl]piperidine dioxalate, m.p. 95°–96° C.

N-(2-Phenoxyethyl)piperidine-3-carbaldehyde a) A mixture of ethyl 3-piperidinecarboxylate (20.58 g), 2-bromoethyl phenyl ether (26.31 g), sodium bicarbonate (10.99 g) and IMS (100 ml) was boiled under reflux for 16 hours. The mixture was evaporated to dryness then diluted with water (100 ml) and 2M sodium hydroxide solution (20 ml). This mixture was extracted with dichloromethane and the combined dichloromethane extracts were extracted with 2M hydrochloric acid. The acidic extracts were washed with dichloromethane and then basified with 2M sodium hydroxide solution. This mixture was extracted with dichloromethane to give ethyl N-(2-phenoxyethyl)piperidine-3-carboxylate as an oil. A sample of the oil was dissolved in ether and ethereal oxalic acid was added. The precipitate was filtered off and recrystallised from aqueous propan-2-ol to give ethyl N-(2-phenoxyethyl)piperidine-3-carboxylate oxalate hemihydrate, m.p. 131°–132° C.

b) Di-isobutylaluminium hydride (13.2 ml of 1.5M solution in toluene) was added to a mixture of ethyl N-(2-phenoxyethyl)piperidine-3-carboxylate (5.0 g) in dry THF (50 ml) at 0° C. under nitrogen with stirring. The mixture was quenched with water (5 ml) and then treated with saturated Rochelles salt solution. The mixture was stirred at room temperature for 30 minutes and then filtered. The filtrate was separated and the organic layer was washed, dried and evaporated to give N-(2-phenoxyethyl)piperidine-3-carbaldehyde as an oil.

3-Chloromethyl-1-(2-phenoxyethyl)piperidine hydrochloride a) A mixture of 2-bromoethyl phenyl ether (20.1 g), piperidin-3-yl-methanol (11.5 g), sodium bicarbonate (8.4 g) and IMS (100 ml) was boiled under reflux for 16 hours. The mixture was evaporated to dryness under reduced pressure and the residue was treated with water (50 ml), 2M sodium hydroxide solution (20 ml) and extracted with dichloromethane. The combined dichloromethane extracts were washed with brine and then extracted with 2M hydrochloric acid. The combined acidic extracts were washed with dichloromethane then basified with 2M sodium hydroxide solution and then extracted with dichloromethane to give 1-(2-phenoxyethyl)piperidin-3-ylmethanol as an oil.

b) A solution of thionyl chloride (1.7 ml) in chloroform (10 ml) was added dropwise with stirring to a solution of 1-(2-phenoxyethyl)piperidin-3-ylmethanol (5.0 g) in chloroform (70 ml) at 0°–5° C. After the addition the mixture was boiled under reflux for 2.5 hours. The solvent was removed under reduced pressure and the residue was triturated with ether and filtered to give 3-chloromethyl-1-(2-phenoxyethyl)piperidine hydrochloride, m.p. 125°–127° C.

PHARMACEUTICAL EXAMPLES

Example U

In the preparation of capsules, 10 parts by weight of active compound and 240 parts by weight of lactose are de-aggregated and blended. The mixture is filled into hard gelatin capsules, each capsule containing 10 mg active compound.

Example V

Tablets are prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tableting machine to give tablets containing 10 mg of active compound.

Example W

Tablets are prepared by the method of the previous Example. The tablets are enteric coated in a conventional manner using a solution of 20% cellulose acetate phthalate and 3% diethyl phthalate in ethanol:dichloromethane (1:1).

Example X

In the preparation of suppositories, 100 parts by weight of active compound is incorporated in 1300 parts by weight of semi-synthetic glycerides as the suppository base and the mixture formed into suppositories each containing 100 mg of active ingredient.

Example Y

In the preparation of capsules, 50 parts by weight of active compound, 300 parts by weight of lactose and 3 parts by weight of magnesium stearate are de-aggregated and blended. The mixture is filled into hard gelatin capsules, each capsule containing 50 mg of active ingredient.

Example Z

The active compound is incorporated into the base by thorough homogenization until the drug is evenly distributed. The ointment is packed into 10 g amber jars with screw-capped lined lids.

| Active compound | 0.1 g |
| --- | --- |
| White soft paraffin | to 10 g |

We claim:

1. Compounds of formula I

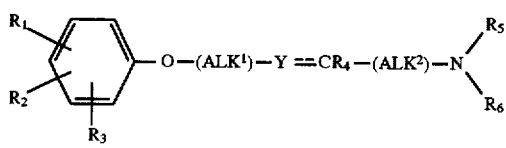

and pharmaceutically acceptable salts thereof in which $R_1$, $R_2$ and $R_3$ independently represent hydrogen, hydroxy, halo and $C_{1-6}$ alkyl group (optionally substituted by one or more halogen atoms) or a $C_{1-6}$ alkoxy group (optionally substituted by one or more halogen atoms);

ALK$^1$ represents a $C_{2-6}$ alkylene chain optionally substituted by one or more $C_{1-2}$ alkyl groups;

Y represents a piperidine ring which is attached through nitrogen to ALK$^1$;

$R_4$ represents hydrogen or a $C_{1-4}$ alkyl group;

the broken line in --- represents a bond, so that a double bond connects Y and $CR_4$, or is absent and the free valency on Y is taken up by hydrogen and the free valency on Y is taken up by hydrogen and the free valency on $C_{1-4}$ is taken up by hydrogen or a $C_{1-4}$ alkyl group;

ALK$^2$ is absent or represents a $C_{1-4}$ alkylene chain optionally substituted by one or more $C_{1-2}$ alkyl groups; and $R_5$ represents hydrogen, a $C_{1-4}$ alkyl group or a phenyl $C_{1-4}$ alkyl group (in which the phenyl ring is optionally substituted by one or more of the following; a $C_{1-4}$ alkyl group, a $C_{1-4}$ alkoxy group or halo); and $R_6$ represents a $C_{1-4}$ alkyl group or a phenyl $C_{1-4}$ alkyl group (in which the phenyl ring is optionally substituted by one or more of the following; a $C_{1-4}$ alkyl group, a $C_{1-4}$ alkoxy group or halo); or $R_5$ and $R_6$ together with the nitrogen atom to which they are attached represents a pyrrolidine ring, a piperidine ring or a morpholine ring.

2. Compounds according to claim 1 as represented by formula II

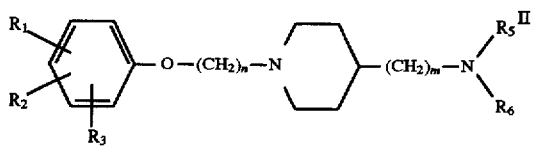

and pharmaceutically acceptable salts thereof in which $R_1$, $R_2$ and $R_3$ independently represent hydrogen, hydroxy, halo, trifluoromethyl, a $C_{1-4}$ alkyl group or a $C_{1-4}$ alkoxy group;

n=2–4 and m=1–3;

$R_5$ represents hydrogen, a $C_{1-4}$ alkyl group or a phenyl $C_{1-4}$ alkyl group (in which the phenyl ring is optionally substituted by one or more of the following: a $C_{1-4}$ alkyl group, a $C_{1-4}$ alkoxy group or halo); and $R_6$ represents a $C_{1-4}$ alkyl group or a phenyl $C_{1-4}$ alkyl group (in which the phenyl ring is optionally substituted by one or more of the following: a $C_{1-4}$ alkyl group, a $C_{1-4}$ alkoxy group or halo);

or $R_5$ and $R_6$ together with the nitrogen atom to which they are attached represent a pyrrolidine ring, a piperidine ring or a morpholine ring.

3. Compounds according to claim 1 as represented by formula III

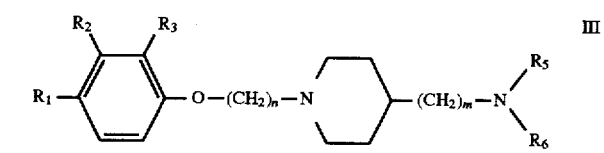

and pharmaceutically acceptable salts thereof in which $R_1$ represents hydrogen, halo, a $C_{1-4}$ alkyl group or a $C_{1-4}$ alkoxy group;

$R_2$ represents hydrogen, halo, a $C_{1-4}$ alkyl group or a $C_{1-4}$ alkoxy group;

n=2 and m=1–3;

$R_3$ represents hydrogen, a $C_{1-4}$ alkoxy group or hydroxy;

$R_5$ represents hydrogen, a $C_{1-4}$ alkyl group or a phenyl $C_{1-4}$ alkyl group (in which the phenyl ring is optionally substituted by one or more of the following: a $C_{1-4}$ alkyl group, a $C_{1-4}$ alkoxy group or halo); and $R_6$ represents a $C_{1-4}$ alkyl group or a phenyl $C_{1-4}$ alkyl group (in which the phenyl ring is optionally substituted by one or more of the following: a $C_{1-4}$ alkyl group, a $C_{1-4}$ alkoxy group or halo);

or $R_5$ and $R_6$ together with the nitrogen atom to which they are attached represent a pyrrolidine ring, a piperidine ring or a morpholine ring.

4. Compounds according to claim 3 in which $R_1$ represents hydrogen, chloro, fluoro, methoxy or methyl.

5. Compounds according to claim 3 in which $R_2$ represents hydrogen or chloro.

6. Compounds according to claim 3 in which $R_3$ represents hydrogen, hydroxy or methoxy.

7. Compounds according to claim 3 in which $R_5$ represents hydrogen, methyl, ethyl or propyl and $R_6$ represents methyl, ethyl, propyl or benzyl or $R_5$ and $R_6$ together with the nitrogen atom to which they are attached represent a pyrrolidine ring or a piperidine ring.

8. Compounds according to claim 3 in which m represents 1.

9. A compound of formula I according to claim 1 selected from:

4-(dimethylaminomethyl)-1-[2-(4-methylphenoxy)ethyl] piperidine;
1-[2-(3-chlorophenoxy)ethyl]-4-(dimethylaminomethyl) piperidine;
4-(N-benzylaminomethyl)-1-(2-phenoxyethyl)piperidine;
4-(N-benzyl-N-methylaminomethyl)-1-(2-phenoxyethyl) piperidine;
4-(dimethylaminomethyl)-1-(2-phenoxyethyl)piperidine;
1-[2-(4-chlorophenoxy)ethyl]-4-(dimethylaminomethyl) piperidine;
4-(dimethylaminomethyl)-1-[2-(4-fluorophenoxy)ethyl] piperidine;
4-(2-dimethylaminoethyl)-1-[2-(4-methylphenoxy)ethyl] piperidine;
4-[2-(N-benzyl-N-methylamino)ethyl]-1-(2-phenoxyethyl) piperidine;
1-(2-phenoxyethyl)-4-(2-piperidinoethyl)piperidine; and
4-(2-dimethylaminoethyl)-1-(2-phenoxyethyl)piperidine.

10. A pharmaceutical composition for oral administration comprising a therapeutically effect amount of a compound of formula I

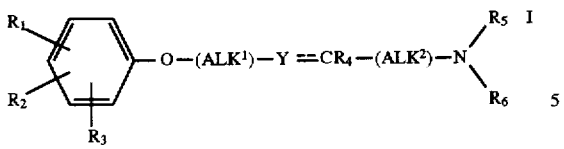

and pharmaceutically acceptable salts thereof in which $R_1$, $R_2$ and $R_3$ independently represent hydrogen, hydroxy, halo and $C_{1-6}$ alkyl group (optionally substituted by one or more halogen atoms) or a $C_{1-6}$ alkoxy group (optionally substituted by one or more halogen atoms);

ALK$^1$ represents a $C_{2-6}$ alkylene chain optionally substituted by one or more $C_{1-2}$ alkyl groups;

Y represents a piperidine ring which is attached through nitrogen to ALK$^1$;

$R_4$ represents hydrogen or a $C_{1-4}$ alkyl group;

the broken line in --- represents a bond, so that a double bond connects Y and CR$_4$ or is absent and the free valency on Y is taken up by hydrogen and the free valency on CR$_4$ is taken up by hydrogen or a $C_{1-4}$ alkyl group;

ALK$^2$ is absent or represents a $C_{1-4}$ alkylene chain optionally substituted by one or more $C_{1-2}$ alkyl groups; and $R_5$ and $R_6$ independently represent hydrogen, a $C_{1-6}$ alkyl group, a phenyl $C_{1-4}$ alkyl group (in which the phenyl ring is optionally substituted by one or more of the following; a $C_{1-4}$ alkyl group, a $C_{1-4}$ alkoxy group, halo or trifluoromethyl) or $R_5$ and $R_6$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups together with a pharmaceutically acceptable diluent or carrier.

11. A method of treating inflammatory and/or alleric conditions and/or diseases with an immunological association comprising the administration of a therapeutically effective amount of a compound of formula I

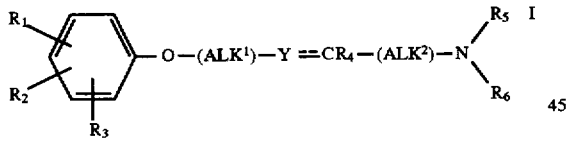

and pharmaceutically acceptable salts thereof in which $R_1$, $R_2$ and $R_3$ independently represent hydrogen, hydroxy, halo, a $C_{1-6}$ alkyl group (optionally substituted by one or more halogen atoms) or a $C_{1-6}$ alkoxy group optionally substituted by one or more halogen atoms);

ALK$^1$ represents a $C_{2-6}$ alkylene chain optionally substituted by one or more $C_{1-2}$ alkyl groups;

Y represents a piperidine ring which is attached through nitrogen to ALK$^1$;

$R_4$ represents hydrogen or a $C_{1-4}$ alkyl group;

the broken line in --- represents a bond, so that a double bond connects Y and CR$_4$, or is absent and the free valency on Y is taken up by hydrogen and the free valency on CR$_4$ is taken up by hydrogen or a $C_{1-4}$ alkyl group:

ALK$^2$ is absent or represents a $C_{1-4}$ alkylene chain optionally substituted by one or more $C_{1-2}$ alkyl groups; and $R_5$ and $R_6$ independently represent hydrogen, a $C_{1-6}$ alkyl group, a phenyl $C_{1-4}$ alkyl group (in which the phenyl ring is optionally substituted by one or more of the following a $C_{1-4}$ alkyl group, a $C_{1-4}$ alkoxy group, halo or trifluoromethy) or $R_5$ and $R_6$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups; to a mammal in need thereof.

12. A process to prepare a compound of formula I according to claim 1 comprising:

a) reacting a compound of formula IV

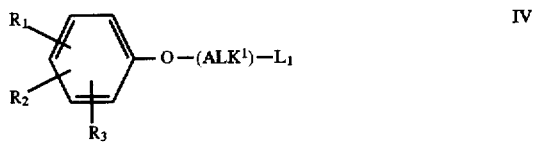

in which $R_1$, $R_2$, $R_3$ and ALK$^1$ are as previously defined and $L_1$ represents a leaving group, with a compound of formula V

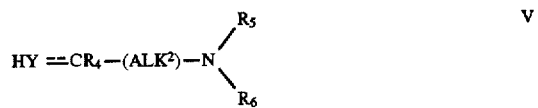

in which Y, $R_4$, ALK$^2$, $R_5$ and $R_6$ are as previously defined, optionally in the presence of an inert organic liquid, at a temperature in the range 0°–250° C., optionally in the presence of a base; or b) reacting a compound of formula VI

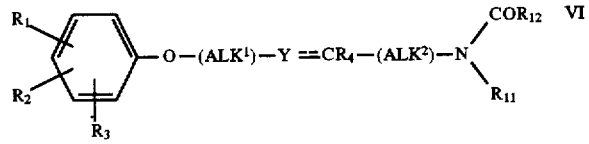

in which $R_1$, $R_2$, $R_3$, ALK$^1$, Y, $R_4$ and ALK$^2$ are as initially defined and $R_{12}$CO represents a group which on reduction yields a group $R_5$ of formula —CH$_2$R$_{12}$ and $R_{11}$ represents $R_6$ (or $R_{12}$CO to give compounds in which $R_5$ and $R_6$ are identical), with a reducing agent, at a temperature in the range from −50° to 200° C., to give compounds of formula I in which $R_5$ represents a group other than hydrogen; or c) reacting a compound of formula VII

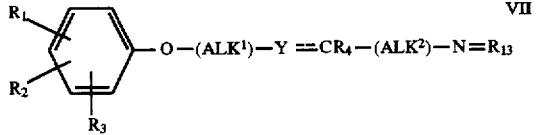

in which $R_1$, $R_2$, $R_3$, ALK$^1$, Y, $R_4$ and ALK$^2$ are as initially defined and —N=$R_{13}$ represents a group which on reduction yields —NHR$_6$, with a reducing agent, at a temperature in the range 0°–200° C., to give compounds of formula I in which $R_5$ represents hydrogen; or d) deprotecting a compound of formula VIII

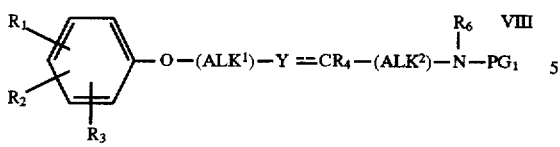

in which $R_1$, $R_2$, $R_3$, $ALK^1$, $Y$, $R_4$, $R_6$ and $ALK^2$ are as initially defined and $PG_1$ represents an amine protecting group to give compounds of formula I in which $R_5$ represents hydrogen; or e) reacting a compound of formula IX

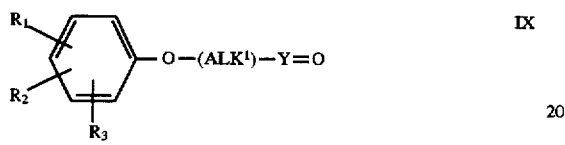

in which $R_1$, $R_2$, $R_3$, $ALK^1$ and $Y$ are as initially defined, with a Wittig reagent, for example (a) a compound of formula Xa

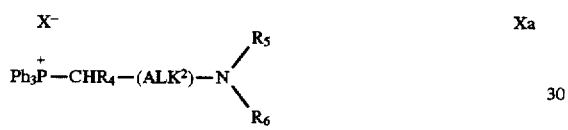

in which $ALK^2$, $R_4$, $R_5$ and $R_6$ are as initially defined and X represents halo.

or (b) a compound of formula Xb

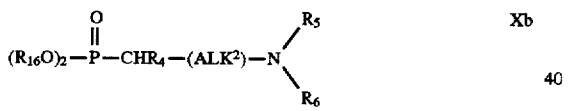

in which $ALK^2$, $R_4$, $R_5$ and $R_6$ are as initially defined and $R_{16}$ represents an alkyl group, in which Xa or Xb has been pretreated with a base, in an inert organic liquid and the mixture combined in an inert organic liquid, at a temperature in the range from 0° C. up to the boiling point of the inert organic liquid, to give compounds of formula I in which ($CR_4$) is connected to Y by a double bond; or f) reducing compounds of formula XI

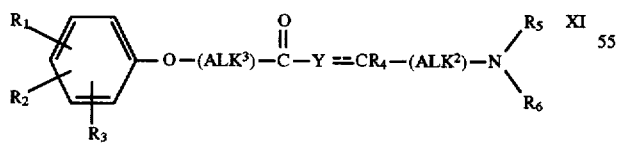

in which $R_1$, $R_2$, $R_3$, $Y$, $R_4$, $ALK^2$, $R_5$ and $R_6$ are as initially defined and —$ALK^3$—CO— represents a group which on reduction yields a group of formula —$ALK^1$—, in an inert organic liquid, at a temperature in the range from 0° C. up to the boiling point of the inert organic liquid; or g) hydrolysing compounds of formula XII

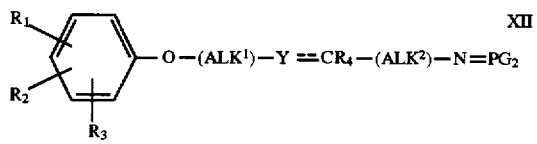

in which $R_1$, $R_2$, $R_3$, $ALK^1$, $R_4$ and $ALK^2$ are as initially defined and $PG_2$ represents an amine protecting group, optionally in the presence of a base, or an acid to give compounds of formula I in which $R_5$ and $R_6$ represent hydrogen at a temperature in the range 0°–250° C.; or h) reducing a compound of formula XIII

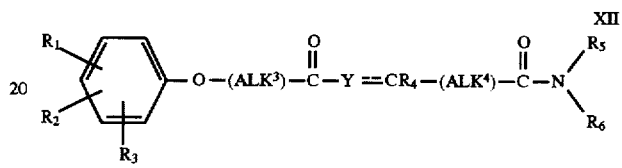

in which $R_1$, $R_2$, $R_3$, $Y$, $R_4$, $R_5$ and $R_6$ are as initially defined and —($ALK^3$)—CO— and ($ALK^4$)—CO— represent groups which on reduction give $ALK^1$ and $ALK^2$ respectively, in an inert organic liquid at a temperature in the range from 0° C. up to the boiling point of the inert organic liquid; or i) reacting a compound of formula XIV

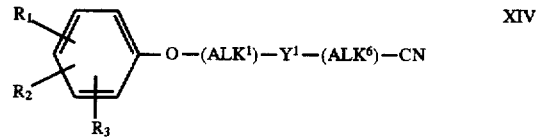

in which $R_1$, $R_2$, $R_3$, $ALK^1$ are as initially defined, $ALK^6$ is absent and $Y^1$ represents a piperidine ring, or a pyridinium ring having a halide counter ion, with a reducing agent, in an inert organic liquid at a temperature in the range from 0° C. up to the boiling point of the inert organic liquid to give compounds of formula I in which —$CR_4$— represents methylene, $ALK^2$ is absent and $R_5$ and $R_6$ represent hydrogen; or j) reacting a compound of formula XIV

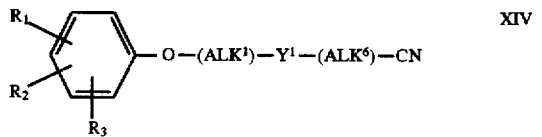

in which —($ALK^6$)—CN represents a group which on reduction gives —$CH(R_4)$—($ALK^2$)—$NH_2$ and $Y^1$ represents a piperidine ring, or a pyridinium ring having a halide counter ion, with a reducing agent, in an inert organic liquid at a temperature in the range from 0° C. up to the boiling point of the inert organic liquid to give compounds of formula I in which the broken line is absent, the free valency on Y is taken up by hydrogen, the free valency on $CR_4$ is taken up by hydrogen or a $C_{1-4}$ alkyl group, $R_5$ and $R_6$ each represent hydrogen and $ALK^2$ represents a $C_{1-4}$ alkylene chain; or k) reacting a compound of formula XV

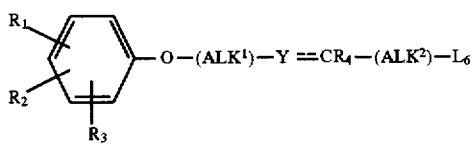

in which $R_1$, $R_2$, $R_3$, $ALK^1$, Y, $R_4$ and $ALK^2$ are as initially defined and $L_6$ represents a leaving group, with a compound of formula XXX

in which $R_5$ and $R_6$ are as initially defined, optionally in the presence of an inert organic liquid at a temperature in the range from 0° C. up to the boiling point of the inert organic liquid; or l) reacting a compound of formula XVI

in which $R_1$, $R_2$ and $R_3$ are as initially defined with a compound of formula XVIII

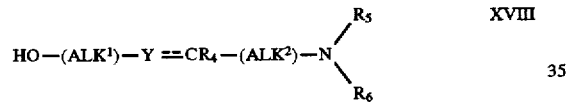

in which $ALK^1$, Y, $R_4$, $ALK^2$, $R_5$ and $R_6$ are as initially defined, in the presence of a dialkyl azodicarboxylate, and a phosphorus (III) reagent, optionally in the presence of an inert organic liquid at a temperature in the range from 0° C. up to the boiling point of the inert organic liquid; or m) reacting compounds of formula XL

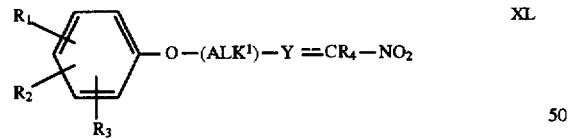

in which $R_1$, $R_2$, $R_3$, $ALK^1$, Y and $R_4$ are as initially defined with a reducing agent to give compounds of formula I in which $R_5$ and $R_6$ each represent hydrogen and $ALK^2$ is absent; or n) reacting a compound of formula V

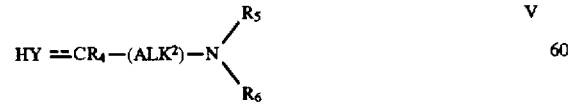

in which Y, $R_4$, $ALK^2$, $R_5$ and $R_6$ are as initially defined with a compound of formula XLI

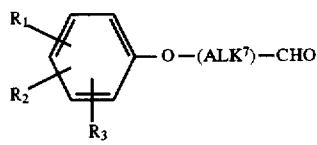

in which $R_1$, $R_2$ and $R_3$ are as initially defined and —(ALK$^7$)—CHO represents a group which on reaction and reduction yields a group of formula $ALK^1$, optionally in the presence of an inert organic liquid at a temperature in the range from 0° C. up to the boiling point of the inert organic liquid followed by reaction of the product with a reducing agent, optionally in the presence of an inert organic liquid at a temperature in the range 0°–250° C.; or o) reacting a compound of formula XVI

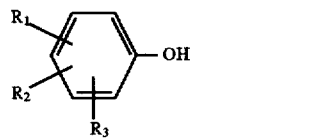

in which $R_1$, $R_2$ and $R_3$ are as initially defined with a compound of formula XLII

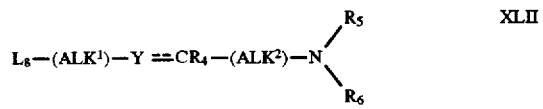

in which $ALK^1$, Y, $R_4$, $ALK^2$, $R_5$ and $R_6$ are as initially defined and $L_8$ represents a leaving group, optionally in the presence of an inert organic liquid at a temperature in the range 0°–250° C., optionally in the presence of a base; or p) alkylating a compound of formula I in which $R_6$ and/or $R_5$, respectively, represents hydrogen either 1) directly using an alkylating agent of formula $R_5L_3$ or $R_6L_3$ in which $L_3$ represents a leaving group in the presence of an organic liquid at a temperature in the range 0°–150° C. optionally in the presence of a base or 2) by reductive alkylation, at a temperature in the range 0°–200° C., optionally in the presence of an inert organic liquid to give compounds of formula I in which $R_5$ and/or $R_6$ represents a group other than hydrogen; or q) hydrogenating a compound of formula I in which $\equiv$ represents a double bond, in the presence of an inert organic liquid, at a temperature in the range 0°–250° C. to give compounds of formula I in which $\equiv$ represents a single bond.

13. 4-(dimethylaminomethyl)-1-(2-phenoxyethyl)-piperidine and pharmaceutically acceptable salts thereof.

14. A pharmaceutical composition comprising a therapeutically effective amount of a compound according to claim 1 together with a pharmaceutically acceptable diluent or carrier.

* * * * *

UNITED STATES PATENT AND TRADEMARK OFFICE
CERTIFICATE OF CORRECTION

PATENT NO.: 5,760,035

DATED: June 2, 1998

INVENTOR(S): RAFFERTY et al.

It is certified that error appears in the above-identified patent and that said Letters Patent is hereby corrected as shown below:

On the cover page, item [30], "[EP] European Patent Off." should be --[DE] Germany--.

Signed and Sealed this

First Day of September, 1998

Attest:

BRUCE LEHMAN

*Attesting Officer*      *Commissioner of Patents and Trademarks*